(12) United States Patent
Schwartzbauer et al.

(10) Patent No.: US 11,317,876 B2
(45) Date of Patent: May 3, 2022

(54) WEIGHTBEARING SIMULATION ASSEMBLY AND METHODS OF USING THE SAME TO IMAGE A SUBJECT

(71) Applicant: SIMULATE Technologies, LLC, Gibsonia, PA (US)

(72) Inventors: Daniel Schwartzbauer, Gibsonia, PA (US); Mark Carl Miller, Oakmont, PA (US); Stephen F. Conti, Sewickley, PA (US)

(73) Assignee: SIMULATE Technologies, LLC, Gibsonia, PA (US)

( * ) Notice: Subject to any disclaimer, the term of this patent is extended or adjusted under 35 U.S.C. 154(b) by 0 days.

(21) Appl. No.: 17/325,532

(22) Filed: May 20, 2021

(65) Prior Publication Data

US 2021/0378605 A1 Dec. 9, 2021

Related U.S. Application Data

(63) Continuation of application No. 16/895,781, filed on Jun. 8, 2020, now Pat. No. 11,013,476.

(51) Int. Cl.
*A61B 6/00* (2006.01)
*A61B 6/03* (2006.01)
*A61B 6/04* (2006.01)

(52) U.S. Cl.
CPC ............ *A61B 6/035* (2013.01); *A61B 6/0414* (2013.01); *A61B 6/0492* (2013.01)

(58) Field of Classification Search
CPC ...... A61B 6/035; A61B 6/0414; A61B 6/0492
See application file for complete search history.

(56) References Cited

U.S. PATENT DOCUMENTS

| 4,829,549 A | 5/1989 | Vogel et al. |
| 5,743,264 A | 4/1998 | Bonuttl |

(Continued)

FOREIGN PATENT DOCUMENTS

| AU | 774376 B2 | 6/2004 |
| CN | 102099708 A | 6/2011 |

(Continued)

OTHER PUBLICATIONS

Campbell et al., Pilot Study of a 3-Dimensional Method for Analysis of Pronation of the First Metatarsal of Halifax Valgus Patients, Article, Published in Sep. 2018, vol. 39(12). 1449-1456, Foot and Ankle Surgery, published by American Orthopaedic Foot & Ankle Society.

(Continued)

*Primary Examiner* — Dani Fox
(74) *Attorney, Agent, or Firm* — Dinsmore & Shohl LLP

(57) ABSTRACT

A weightbearing simulation assembly includes a substrate comprising a mounting surface extending in a first direction a subject support disposed on a first region of the mounting surface and a pedal assembly disposed on a second region of the mounting surface. The pedal assembly includes a spring assembly including a contact plate facing the subject support, a compression plate, and a first spring disposed between the contact plate and the compression plate. A subject applies a compressive force to the contact plate in a compression direction to simulate a load-bearing condition by compressing the first spring. An orientation of the pedal assembly may be adjusted to change a relative angle between the compression direction and the first direction to alter an imaging angle.

20 Claims, 18 Drawing Sheets

(56) References Cited

U.S. PATENT DOCUMENTS

| | | | |
|---|---|---|---|
| 7,394,888 B2* | 7/2008 | Sukovic | A61B 6/032 378/20 |
| D667,119 S | 9/2012 | Wodecki | |
| D667,120 S | 9/2012 | Personnelli | |
| 9,808,211 B2 | 11/2017 | Yorkston et al. | |
| 10,092,409 B2 | 10/2018 | Feldman | |
| 2002/0193683 A1* | 12/2002 | Danielsson | A61B 5/055 600/411 |
| 2005/0053185 A1 | 3/2005 | Sukovic et al. | |
| 2005/0053186 A1 | 3/2005 | Sukovic et al. | |
| 2010/0278300 A1 | 11/2010 | Yorkston et al. | |
| 2011/0228901 A1 | 9/2011 | Yorkston et al. | |
| 2015/0272516 A1 | 10/2015 | Litzenberger et al. | |

FOREIGN PATENT DOCUMENTS

| | | |
|---|---|---|
| CN | 102670228 A | 9/2012 |
| CN | 107638190 A | 1/2018 |
| DE | 10146915 A1 | 4/2003 |
| EP | 3332707 A1 | 6/2018 |
| FI | 125528 B | 11/2015 |
| FI | 125530 B | 11/2015 |
| FI | 125531 B | 11/2015 |
| KR | 101885716 B1 | 8/2018 |
| WO | 2005102173 A1 | 11/2005 |
| WO | 2006011942 A1 | 2/2006 |

OTHER PUBLICATIONS

Fadle et al., A simple foot pedal device in a horizontal bore imaging facility replicates weightbearing outcomes for Hallux Valgus patients, Article in Press, Apr. 9, 2019, G Modul FAS 1298, pp. 1-5, Foot and Ankle Surgery, Published by Elsevier www.elsevier.com/locate/fas.

* cited by examiner

WEIGHTBEARING SIMULATION ASSEMBLY AND METHODS OF USING THE SAME TO IMAGE A SUBJECT

CROSS REFERENCE TO RELATED APPLICATIONS

This application is a continuation application of and claims priority to and the benefit of U.S. Non-Provisional application Ser. No. 16/895,781, filed Jun. 8, 2020, the contents of which is hereby incorporated by reference in their entirety.

BACKGROUND

Field

The present application generally relates to medical imaging and, more particularly, to devices and methods for simulating weightbearing conditions to generate medical images of subjects' lower extremities via various modalities, such computed tomography or magnetic resonance tomography.

Technical Background

In order to accurately assess a subject's lower extremities (e.g., hip, knee, foot, ankle, or the like) to plan treatment for conditions therein, it is beneficial to obtain structural measurements of the subject's lower extremities. For certain conditions (e.g., Hallux valgus), it is beneficial to obtain three-dimensional structural measurements of the subject in a loadbearing condition. Existing three-dimensional medical imaging systems (e.g., computed tomography scanners and magnetic resonance imaging systems) present various constraints for creating such a loadbearing condition during imaging to obtain three-dimensional structural measurements. For example, existing bore scanners commonly extend in a horizontal direction, rendering gravity unavailable to supply a normal load to the subject's foot during imaging. Further, existing vertical bore scanners that allow a subject to stand while scanning is completed are extremely expensive, difficult to use, and do not enjoy widespread adoption.

SUMMARY

According to an embodiment of the present disclosure a weightbearing simulation assembly includes a substrate including a mounting surface extending in a first direction; a subject support disposed on a first region of the mounting surface; and a pedal assembly disposed on a second region of the mounting surface. The pedal assembly is spaced apart from the subject support by a distance in the first direction. The pedal assembly includes a spring assembly comprising a contact plate facing the subject support, a compression plate, and a first spring disposed between the contact plate and the compression plate, the spring extending in a compression direction. The pedal assembly also includes a first motion limiter extending through the compression plate, an end of the first motion limiter is disposed between the compression plate and the contact plate to limit a range of motion of the contact plate in the compression direction. The contact plate contacts the first motion limiter at an end of the range of motion to place the first spring into a loaded state when a subject applies a compressive force to the contact plate. The pedal assembly also includes a pedal support assembly disposed on the mounting surface, the pedal support assembly defining a cavity in which the spring assembly is disposed. The pedal assembly also includes an adjustable support element for the pedal support assembly, the adjustable support element includes a plurality of support positions selectable to adjust an orientation of the pedal support assembly to change a relative angle between the compression direction and the first direction.

In another embodiment, a subject imaging assembly includes a support platform extending in a first direction, the support platform including an engagement element. The subject imaging assembly also includes an imaging system including a gantry, the gantry including an opening. The subject imaging assembly also includes a weightbearing simulation assembly disposed on the support platform, the weightbearing simulation assembly includes a substrate coupled to the engagement element of the support platform, the substrate including a mounting surface extending in the first direction. The weightbearing simulation assembly also includes a subject support disposed on a first region of the mounting surface, the subject support rotatable about an axis of rotation to facilitate positioning the subject support relative to the gantry. The weightbearing simulation assembly also includes a pedal assembly disposed on a second region of the mounting surface, n the pedal assembly is spaced apart from the subject support by a distance in the first direction. The pedal assembly includes a spring assembly comprising a contact plate facing the subject support, a compression plate, and a spring disposed between the contact plate and the compression plate, the spring extending in a compression direction and a motion limiter extending from the compression plate. An end of the motion limiter is disposed between the compression plate and the carrier plate to limit a range of motion of the contact plate in the compression direction. The pedal assembly also includes a pedal support assembly disposed on the mounting surface, the pedal support assembly supporting the spring assembly on the mounting surface. The subject imaging assembly further includes an actuator coupled to the substrate of the weightbearing simulation assembly, the actuator configured to move the weightbearing simulation assembly in the first direction such that the pedal assembly is disposed within the opening to generate an image.

In another embodiment, a method of capturing an image of a lower extremity of a subject includes positioning a subject on a subject support of a weight simulation assembly disposed on a support platform of an imaging system. The weight simulation assembly comprises a substrate extending in the first direction, a subject support disposed on a first region of the substrate, and a pedal assembly disposed on a second region of the substrate. The pedal assembly is spaced apart from the subject support by a distance in the first direction. The method also includes adjusting a motion limiter disposed between a contact plate facing the subject support and a compression plate of the pedal assembly so as to change a range of motion of the contact plate within the pedal assembly in a compression direction and create a load tailored to the subject when the contact plate is in a fully pressed position. The method also includes adjusting a relative angle between the compression direction and the first direction so as to adjust an angle of the lower extremity in the pedal assembly. The method also includes positioning the weightbearing simulation assembly relative to a gantry of an imaging system such that the pedal assembly is disposed within an opening of the gantry. The method also includes, once the subject applies the load tailored to the subject to the contact plate via the lower extremity so as to bring the contact plate in contact with the motion limiter, capturing an image of the lower extremity using the imaging system.

Additional features and advantages of the processes and systems described herein will be set forth in the detailed description which follows, and in part will be readily apparent to those skilled in the art from that description or recognized by practicing the embodiments described herein, comprising the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are comprised to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
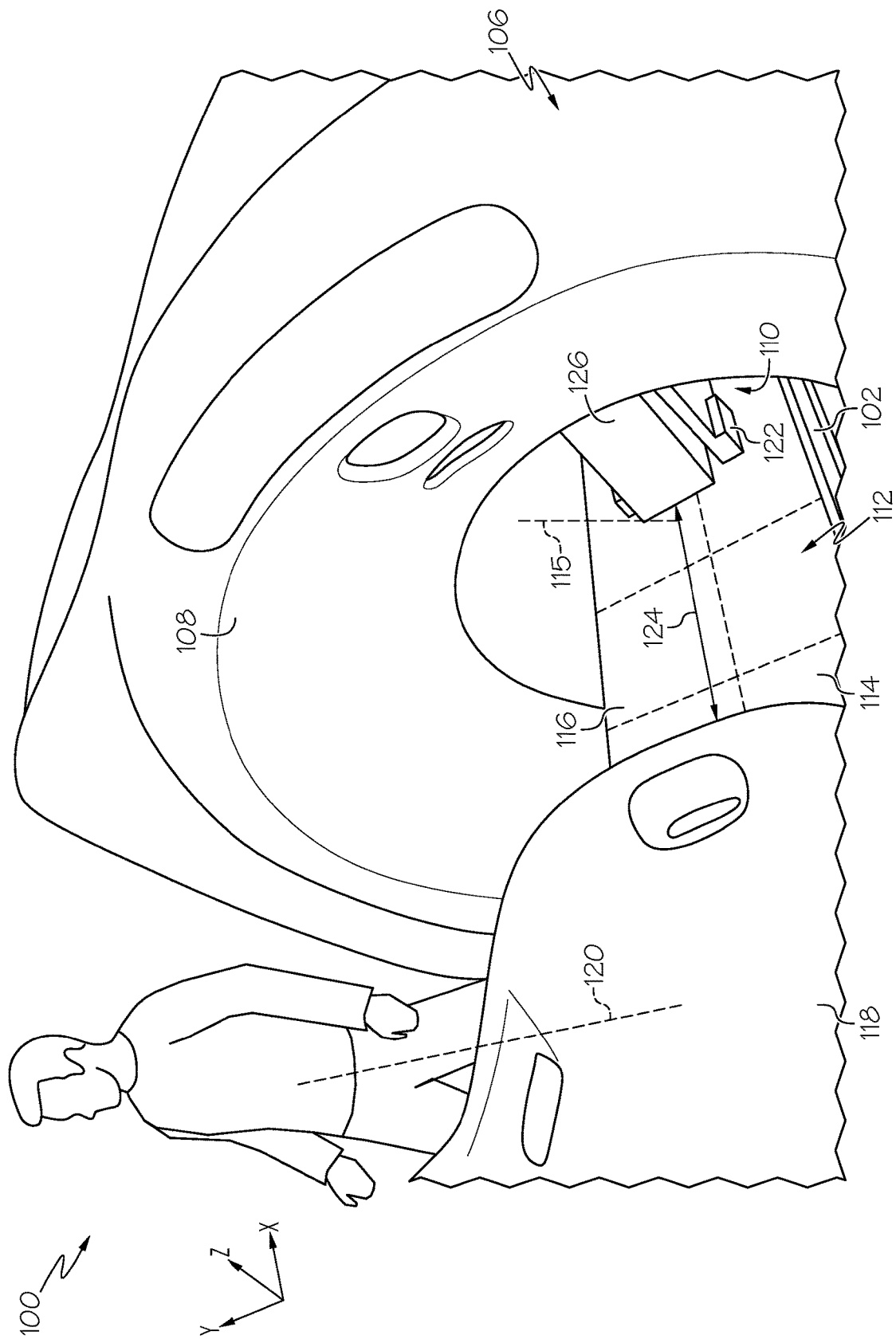
FIG. 1A depicts a perspective view of a subject imaging assembly, according to one or more embodiments described herein.

Reference will now be made in detail to embodiments of a weightbearing simulation assembly for imaging a lower extremity (e.g., a foot, an ankle, a leg, a knee, a hip, or the like) of a subject and methods for using the same for imaging a subject. The weightbearing simulation assembly may include a substrate on which a subject support and a pedal assembly are disposed. In embodiments, the substrate of the weightbearing simulation assembly is disposed on a support platform of a subject imaging assembly. The subject imaging assembly may include an imaging system such as a computer tomography (CT) scanner or a magnetic resonance imaging (MRI) system. The relative positioning of the weightbearing simulation assembly and the imaging system may be adjustable (e.g., via an actuator of the support platform) such that the pedal assembly may be movable to a field of view of the imaging system. In embodiments, the pedal assembly includes a spring assembly including a contact plate facing the subject support and a compression plate separated by at least one spring member.

In an aspect of the present disclosure, the subject supplies a compressive force to the pedal assembly to place the pedal assembly in an imaging position. In response to the subject supplying the compressive force to compress the spring member, the contact plate moves in a compression direction until the contact plate contacts motion limiters of the spring assembly disposed between the contact plate and the compression plate. Once the contact plate contacts the motion limiter, the contact plate is disposed an imaging distance from the compression plate. The spring member supplies resistance to the subject so as to measure the force provided by the subject. In embodiments, the motion limiters are adjustable so as to change the imaging distance and the resistance supplied by the at least one spring member in the presence of the compressive force supplied by the subject. In embodiments, the resistance supplied by the spring member may be individually tailored to the subject to simulate a weightbearing condition for the subject for capturing an image of the subject's lower extremities. Beneficially, the motion limiters provide a visual indication of whether the subject has supplied an adequate compressive force to simulate a weightbearing condition. Additionally, the motion limiters may be distributed to ensure that the subject properly distributes the compressive force throughout an entirety of the subject's foot, preventing the subject from applying too much force using one area of the foot (e.g., a heel) and too little force with another (e.g., a forefoot).

The weightbearing simulation assembly described herein is adaptable to various different imaging positions. For example, the pedal assembly described herein includes a pedal support assembly supporting the spring assembly and an adjustable support element coupling the pedal support assembly to the substrate of the weightbearing simulation assembly. The adjustable support element may include a plurality of support positions to support the pedal support assembly at various orientations. In embodiments, selection among the different orientations alters a relative angle between the compression direction of the spring assembly and an axis of the imaging system to change an angle of the subject's foot included in captured images. The plurality of support positions of the adjustable support element may facilitate capturing images of a subject's ankle, forefoot, and hindfoot with predetermined loads applied to each thereof.

Additionally, the subject support may be configurable for a plurality of different imaging situations. For example, in embodiments, the subject support is rotatably coupled to the substrate such that the subject support is rotatable about a first axis of rotation that is substantially parallel to a surface normal of the substrate to facilitate positioning the subject on the weightbearing simulation assembly. In embodiments, the subject support is also rotatable about a second axis of rotation that is substantially perpendicular to the first axis of rotation to facilitate tilting the positioned patent with respect to the imaging system to facilitate the imaging system being tilted at various angles for additional imaging flexibility. Moreover, the subject support may also be attached to the substrate via a translation support mechanism facilitating adjusting a distance between the pedal assembly and the subject support for accommodating subjects having different leg lengths. As such, the weightbearing simulation assemblies described herein facilitate capturing a plurality of different load-bearing images of the subject's lower extremities in a manner particularly tailored to the subject, thus capturing a complete three-dimensional image for diagnosis and treatment of various conditions.

Beneficially, the weightbearing simulation assemblies described herein require a subject to supply a compressive force to a pedal assembly with a specified foot (e.g., a foot causing the subject discomfort). By providing an indication (e.g., the contact plate contacting the motion limiter) that the subject has supplied a desired amount compressive force, the weightbearing simulation assemblies described herein prevent the subject from off-loading from the specified foot in order to ensure that the specified foot is under a true weightbearing condition. Such a weightbearing condition beneficially facilitates the components of subject's foot being accurately imaged in a functional state. Moreover, compatibility with existing horizontal CT scanners enables three-dimensional functional imaging of the subject's foot at relatively low cost for diagnosing subject foot conditions as compared to existing weightbearing CT scanners. Additionally, the approaches described herein are beneficial over existing weightbearing x-ray imaging techniques because the weightbearing simulation assemblies described herein facilitate weightbearing imaging with three-dimensional modalities (e.g., CT scanning, MRI, etc.).

Figure 1B:
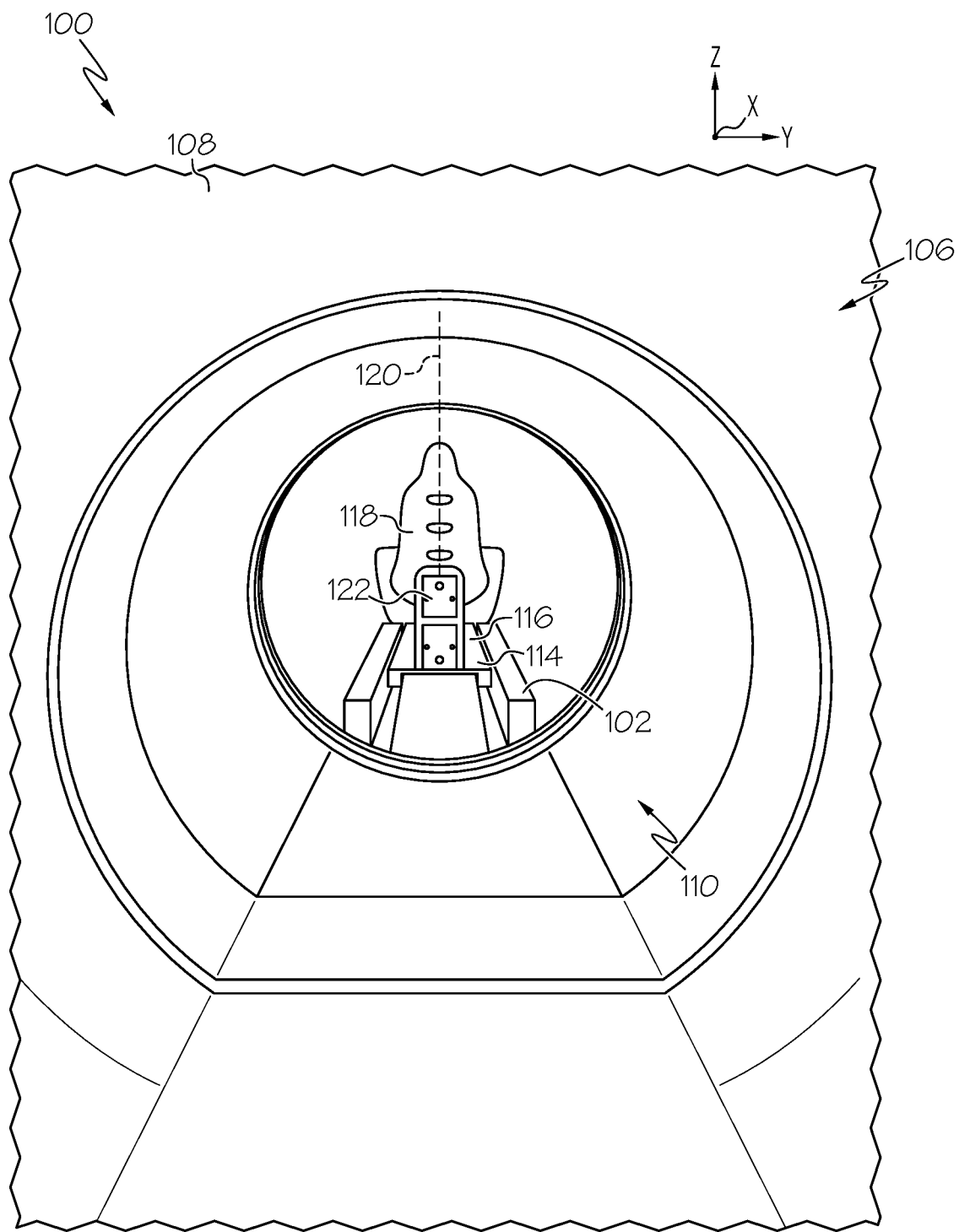
FIG. 1B depicts another perspective view of the subject imaging assembly shown in FIG. 1A, according to one or more embodiments described herein.
Figure 1C:
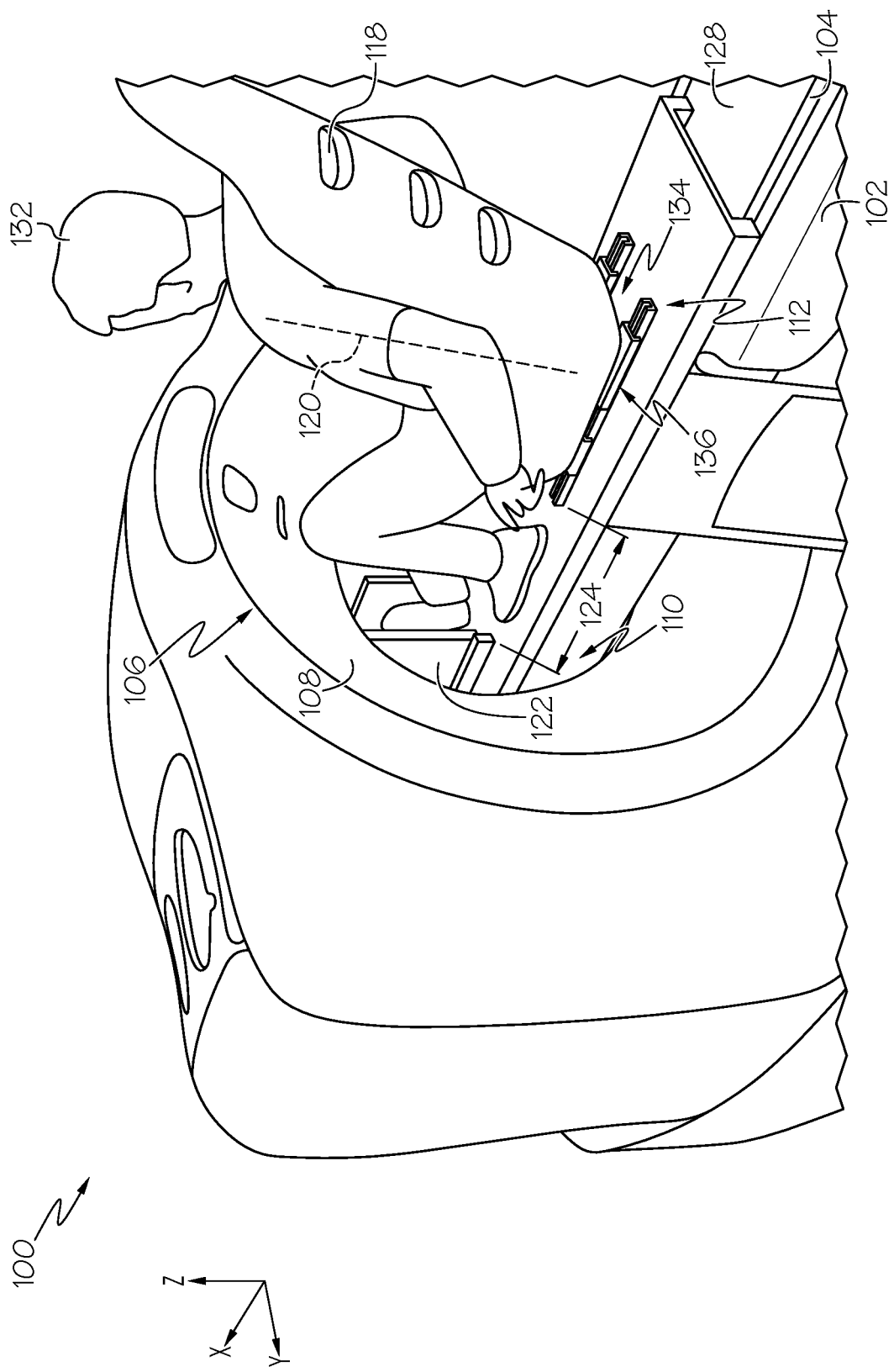
FIG. 1C depicts another perspective view of the subject imaging assembly shown in FIG. 1A with a subject positioned thereon, according to one or more embodiments described herein.

Referring now to FIGS. 1A-1C, a subject imaging assembly 100 is depicted. The subject imaging assembly 100 is depicted to include a support platform 102, an imaging system 106, and a weightbearing simulation assembly 112. In embodiments, the support platform 102 and the imaging system 106 may be derived from an existing medical imaging system such as a computed tomography (CT) scanner or a magnetic resonance imaging (MRI) system. For example, in embodiments, the support platform 102 may comprise a table top of an existing CT scanner with the bedding removed to provide a surface for attaching the weightbearing simulation assembly 112. As depicted in FIG. 1C, the support platform 102 comprises an engagement element 104 that couples to a complementary element of the weightbearing simulation assembly 112. The engagement element 104 comprises a channel (or a plurality of channels) adapted to receive a substrate 114 of the weightbearing simulation assembly 112. It should be appreciated that the support platform 102, the engagement element 104, and the complementary element of the substrate 114 may take a variety of forms depending on the implementation. The weightbearing simulation assembly 112 and the associated substrate 114 may be adapted to fit to any available subject imaging system. As such, the dimensions of the substrate 114 and any mechanisms incorporated in the weightbearing simulation assembly 112 for attaching the substrate 114 to the support platform 102 may vary depending on the subject imaging system into which the weightbearing simulation assembly 112 is being incorporated.

The support platform 102 and substrate 114 of the weightbearing simulation assembly 112 both extend in a first direction (e.g., the x-direction of the coordinate axes shown in FIGS. 1A-1C). As depicted in FIG. 1B, the support platform 102 is substantially aligned with an opening 110 of a gantry 108 of the imaging system 106. In embodiments, the imaging system 106 comprises an imaging axis (not depicted) extending in the first direction through the opening 110. In embodiments, the gantry 108 includes a radiation source (e.g., an x-ray source, not depicted) that transmits radiation through the opening 110 and a detector (not depicted) for detecting the radiation transmitted through a subject (e.g., a subject 132) disposed in the opening 110 (See FIG. 1C). The radiation source and detector may be disposed in a rotating ring (not depicted) of the gantry 108 that rotates about the imaging axis to generate a three-dimensional image of the subject based on the radiation transmitted through the subject. In embodiments, the imaging system 106 comprises a CT scanner or an MRI system.

In embodiments, the support platform 102 comprises an actuator 128 (see FIG. 1C) adapted to translate an element (e.g., the substrate 114 of the weightbearing simulation assembly 112) in the first direction. The actuator 128 may comprise any mechanism capable of providing relative motion between the weightbearing simulation assembly 112 and the imaging system 106 in the first direction. For example, in embodiments, the actuator 128 is an element (not depicted) that translates within the engagement element 104 to press against the substrate 114 with sufficient force move the substrate 114 in the first direction with a subject 132 disposed thereon. With such movements, the substrate 114 may move in the first direction such that a portion of the substrate 114 is supported within the opening 110 such that a pedal assembly 122 of the weightbearing simulation assembly 112 is disposed within a field of view of the imaging system 106 to capture an image of a lower extremity of the subject 132. In embodiments, the support platform 102 comprises an entire portion (e.g., tabletop) including the engagement element 104 that is movable in the first direction such that a combination of the portion of the support platform 102 and the weightbearing simulation assembly 112 is moved into the opening 110. It should be appreciated that certain embodiments may not include a support platform 102. For example, in such embodiments, the weightbearing simulation assembly 112 may be disposed on a support (e.g., a cart) that is completely separate from the imaging system 106.

The weightbearing simulation assembly 112 comprises a substrate 114 having a mounting surface 116, a subject support 118 disposed on the mounting surface 116 and a pedal assembly 122 disposed on the mounting surface 116. The subject support 118 is separated from the pedal assembly 122 by a distance 124 in the first direction. In embodiments, the substrate 114 is constructed of a material (e.g., carbon fiber) that does not interfere with the imaging capabilities of the imaging system 106. As described herein, the substrate 114 may possess any size, shape, and configuration based on specifications of the incorporating imaging system 106.

As depicted in FIG. 1C, in embodiments, the subject support 118 is coupled to the mounting surface 116 via a translation support mechanism 134 such that the distance 124 between the pedal assembly 122 and the subject support 118 is adjustable to accommodate different subjects 132. The translation support mechanism 134 includes one or more tracks (e.g., a pair of tracks) that mate with corresponding mounting brackets 136 of the subject support 118. In embodiments, fasteners (not depicted) coupling the mounting brackets 136 to the translation support mechanism 134 may be loosened and the distance 124 may be manually adjusted to a particular subject 132. Alternative translation support mechanisms 134 are envisioned. In embodiments, the translation support mechanism 134 comprises an actuator (e.g., a translation stage) coupling the subject support 118 to the mounting surface 116 such that the distance 124 may be adjusted electronically. In embodiments, the translation support mechanism 134 is disposed on a mounting platform (not depicted) attached to the substrate 114. The mounting platform may be movable (e.g., via a telescoping arm or the like) in a second direction (e.g., the z-direction depicted in FIG. 1C) substantially perpendicular to the first direction.

In embodiments, the subject support 118 may be rotatably coupled to the translation support mechanism 134. For example, in embodiments, the translation support mechanism 134 includes a mounting platform (not depicted) to which the subject support 118 is attached. The mounting platform may be rotatable with respect to the remainder of the translation support mechanism 134 such that the subject support 118 is rotatable about first axis of rotation 120 that extends substantially perpendicular (e.g., in the z-direction of the coordinate axes depicted in FIGS. 1A-1C) to the first direction. Such rotation may facilitate positioning (e.g., seating) the subject on the subject support 118. After the subject 132 is initially positioned on the subject support 118, the subject support 118 may be rotated such that a leg of the subject 132 (e.g., after the foot of the subject 132 is positioned on the pedal assembly 122) is aligned in the first direction for imaging. In embodiments, the subject support 118 is rotatable about a second axis of rotation (not depicted) that is substantially perpendicular to the first axis of rotation 120 (e.g., in the y-direction of the coordinate axes depicted in FIGS. 1A-1C) to facilitate tilting the subject relative to the gantry 108 so that the gantry 108 does not contact the subject 132 when rotated about a rotation axis extending in the y-direction.

In embodiments, the subject support 118 is coupled to the translation support mechanism 134 via a height adjusting element (not depicted). In embodiments, the height adjusting element may be similar in structure to the height adjusting element 536 described herein with respect to FIG. 5B. Adjustment of the distance between the subject support 118 and the mounting surface 116 facilitates the subject 132 supplying a compressive force to the pedal assembly 122 when the foot of the subject is placed at an angle to a surface normal 115 (see FIG. 1A) of the mounting surface 116.

In embodiments, the distance between the subject support 118 and the mounting surface 116 is adjusted to particular values depending on a relative angle at which the foot of the subject 132 extends relative to the surface normal 115. For example, in embodiments, the pedal assembly 122 may be adjusted such that the foot of the subject 132 may extend at an angle at 0 degrees, 15 degrees, 30 degrees, 45 degrees, and 60 degrees relative to the surface normal 115. The surface normal 115 may coincide with an imaging axis of the imaging system 106 such that altering the angle of the foot of the subject 132 facilitates imaging different cross-sections of the foot. If the foot is positioned on the pedal assembly 122 such that the foot extends at a 0 degree angle relative to the surface normal 115, the height adjustment element may be adjusted to possess a minimal length such that the distance between the subject support 118 and the mounting surface 116 is at a minimum. If the foot is positioned on the pedal assembly 122 such that the foot extends at a 15 degree angle relative to the surface normal 115, the height adjustment element may be adjusted to possess first length that is greater than the minimal length so that the subject 132 is positioned some distance above the mounting surface 116. If the foot is positioned on the pedal assembly 122 such that the foot extends at a 30 degree angle relative to the surface normal 115, the height adjustment element may be adjusted to possess second length that is greater than the first length, and so on. In embodiments, users of the subject imaging assembly 100 may be instructed to adjust the distance between the subject support 118 and the mounting surface 116 based on the relative angle of the foot based on a color coding scheme or the like.

The pedal assembly 122 receives a compressive force supplied via a lower extremity of the subject 132 and provides resistance in response to the compressive force to simulate a loadbearing condition for the subject 132. In embodiments, the pedal assembly 122 comprises an adjustable spring assembly (not depicted) that provides an adjustable amount of resistance that is specifically tailored to the subject to ensure that the subject supplies an adequate amount of compressive force to the pedal assembly 122 to simulate a weightbearing condition for the subject 132. For example, in embodiments, the pedal assembly 122 may be adjusted such that the subject 132 needs to supply a compressive force corresponding to approximately half of the weight of the subject 132 in order to place the pedal assembly 122 into an imaging state for an image to be captured. More details regarding the various components of a potential implementation of the pedal assembly 122 are provided herein with respect to FIGS. 6A-6F.

Figure 2:
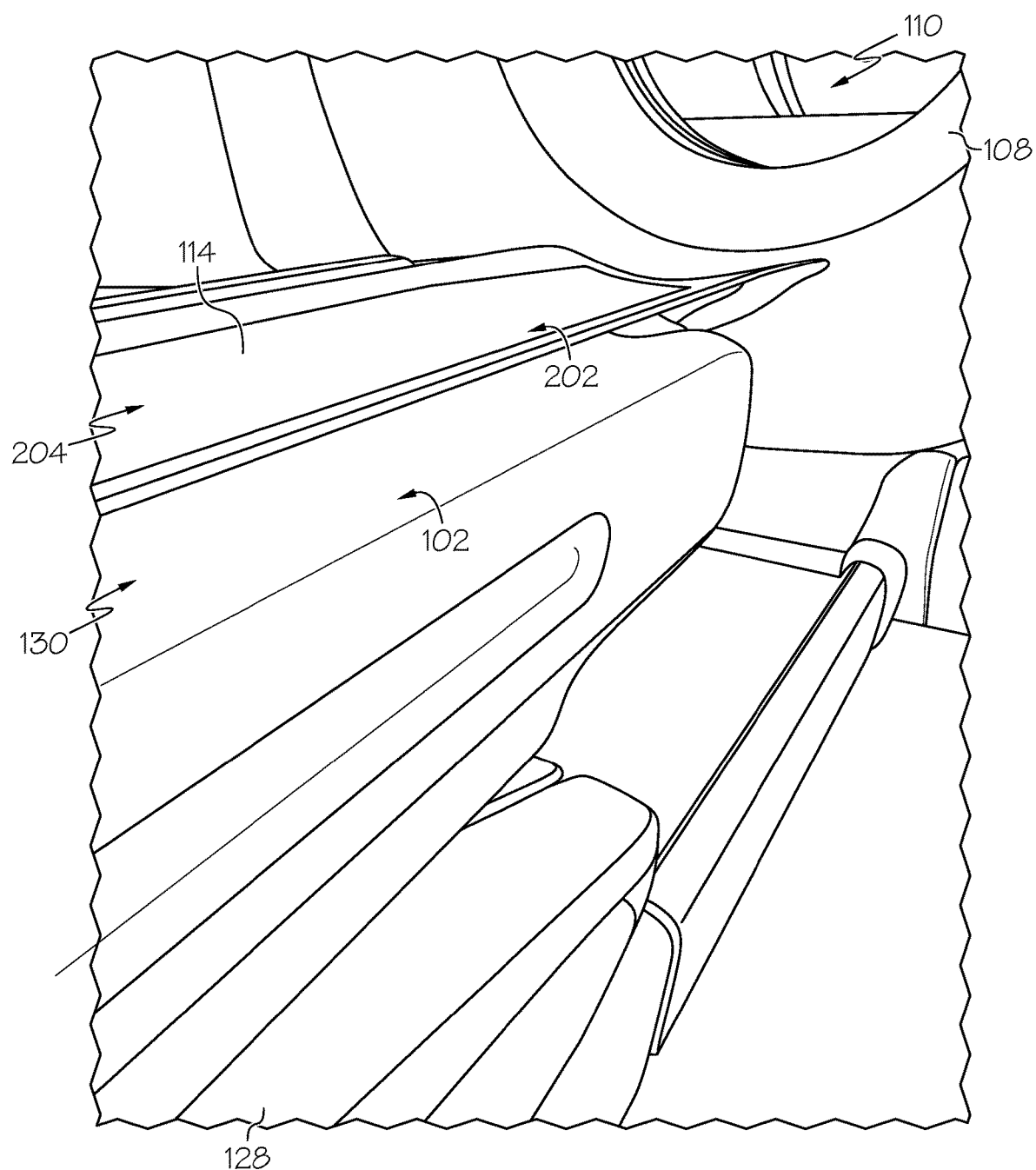
FIG. 2 depicts a perspective view of a support platform of a subject imaging assembly supporting a substrate of a weightbearing simulation assembly, according to one or more embodiments described herein.

As described herein, the substrate 114 and the support platform 102 may take various forms depending on the implementation. For example, FIG. 2 depicts a perspective view of an alternative configuration for the support platform 102 and the substrate 114 described herein with respect to FIGS. 1A, 1B, and 1C. As shown, the support platform 102 is supported by the actuator 128. The actuator 128 is a support arm vertically movable (e.g., in the z-direction described with respect to FIGS. 1A, 1B, and 1C) with respect to the imaging system 106. As depicted, via the actuator 128, the support platform 102 may be positioned such that a support surface 130 thereof is disposed beneath the opening 110 of the gantry 108. Such a positioning of the support platform 102 may facilitate positioning the subject on the support platform 102.

The substrate 114 directly contacts the support surface 130 of the support platform 102. For example, the substrate 114 may be mounted to the support surface 130 via a recess (not depicted) in the support platform 102 that is covered by the substrate 114. As described herein, the actuator 128 may include a movable element (not depicted) that engages with the substrate 114 so as to render the substrate 114 movable toward the gantry 108. In embodiments, after a subject is positioned on the substrate 114 (or a subject support disposed thereon), the actuator 128 may vertically position the substrate 114 such that the substrate 114 is aligned with the opening 110 in the gantry 108 and then move the substrate 114 towards the gantry 108 such that a portion of the substrate 114 is disposed within the opening 110 for imaging a lower extremity of a subject.

The substrate 114 may be attached to the support platform 102 via a plurality of different mechanisms. For example, in embodiments, the substrate 114 may be coupled to the support platform 102 by any of a number of different attachment mechanisms at a first end 202 of the substrate 114 and at a second end 204 of the substrate 114. As depicted, the first end 202 of the substrate 114 is a proximal end disposed near the gantry 108, while the second end 204 is a distal end disposed on the support platform 102.

Figure 3A:
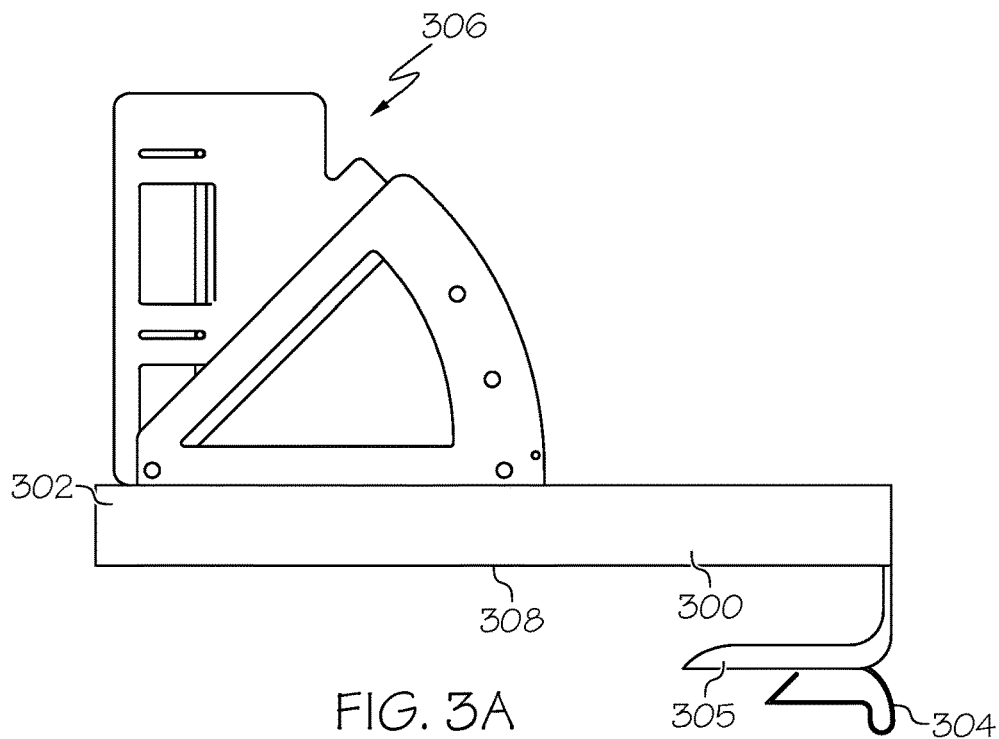
FIG. 3A depicts a perspective view of a substrate of a weightbearing simulation assembly including a mounting element, according to one or more embodiments described herein.
Figure 3B:
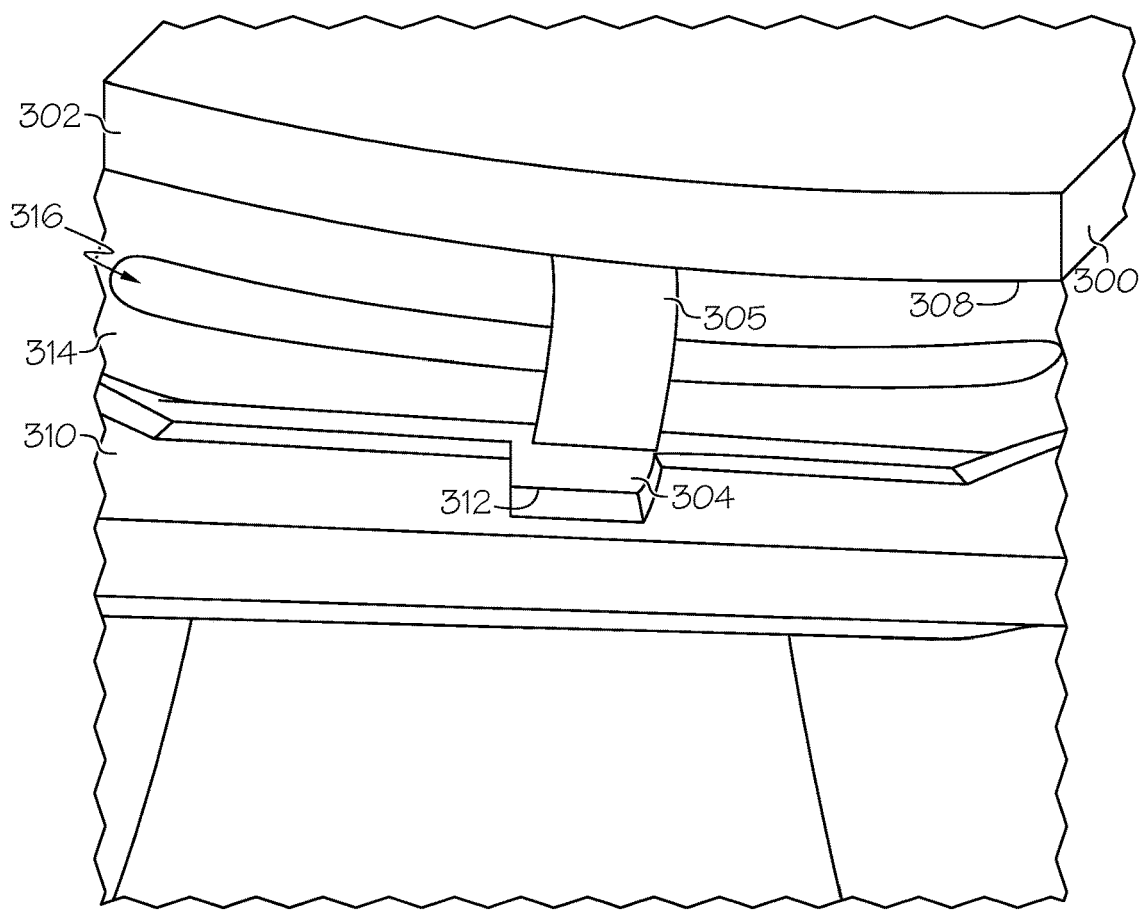
FIG. 3B depicts a perspective view of the substrate depicted in FIG. 3A attached to a support platform of a subject imaging assembly via the mounting element, according to one or more embodiments described herein.

FIG. 3A depicts a side view of a proximal end 302 of a substrate 300. A pedal assembly 306 is disposed on the substrate 300 at the proximal end 302. A clip member 304 is attached to an underside surface 308 of the substrate 300 via an extension clip 305. In embodiments, the clip member 304 is adapted to be inserted into a corresponding attachment element (e.g., a cavity or recess) in a support platform, while the extension clip 305 may be attached to an actuating element of the support platform. For example, FIG. 3B depicts a perspective view of the proximal end 302 of the substrate 300 attached to a support platform 310 of an imaging system. As depicted, the substrate 300 may be disposed on an actuating element 314 (e.g., a support table, a scanner bed, etc.) of the imaging system. The actuating element 314 may include an opening 316 for insertion the extension clip 305. In embodiments, the clip member 304 extends over the actuating element 314 and is inserted into an attachment channel 312 of the support platform 310. As such, via the clip member 304, the substrate 300 is secured to the support platform 310 in a position proximate to the pedal assembly 306 (not depicted in FIG. 3B).

Figure 4A:
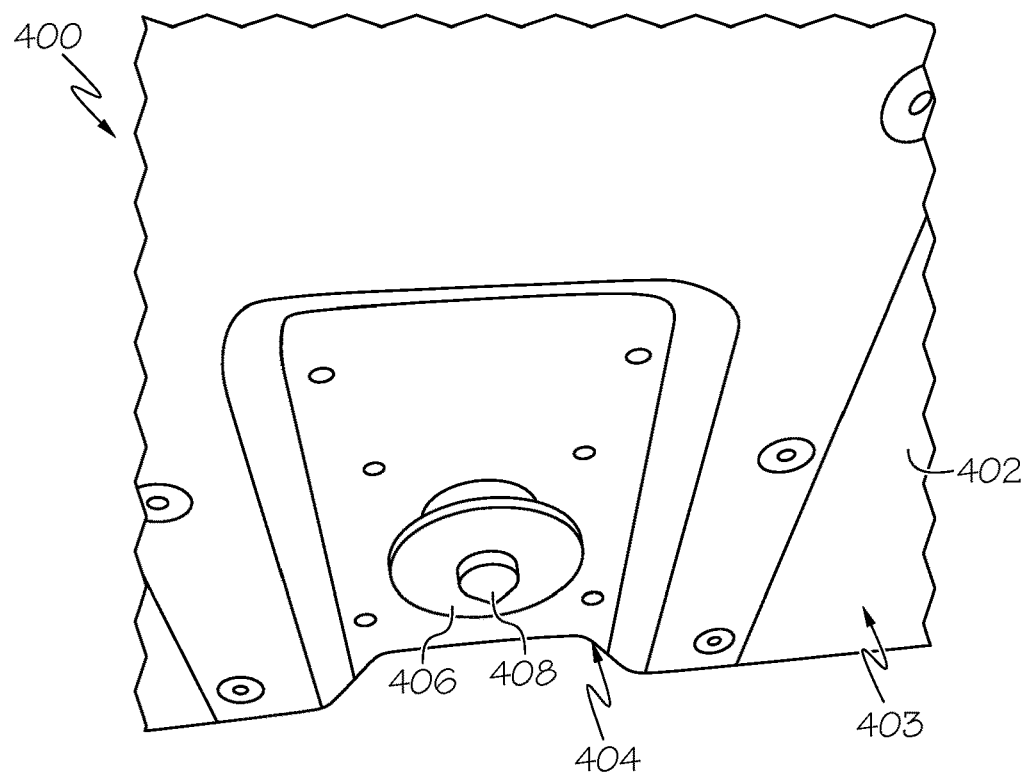
FIG. 4A depicts a perspective view of an underside surface of a substrate of a weightbearing simulation assembly including an attachment element, according to one or more embodiments described herein.

FIG. 4A depicts an example view of a distal end 402 of a substrate 400 of a weightbearing simulation assembly. In embodiments, a subject support (e.g., the subject support 118 described herein with respect to FIGS. 1A, 1B, and 1C) is disposed on the substrate 400 at the distal end 402. An underside surface 403 of the substrate 400 includes a recessed mounting member 404 that includes a mounting peg 406. The mounting peg 406 is a substantially circular member that may be screwed into an underside surface 403. The mounting peg 406 includes a mounting protrusion 408 extending therefrom. In embodiments, the recessed mounting member 404 is adapted to be inserted into a corresponding attachment element of a support platform of a subject imaging assembly.

Figure 4B:
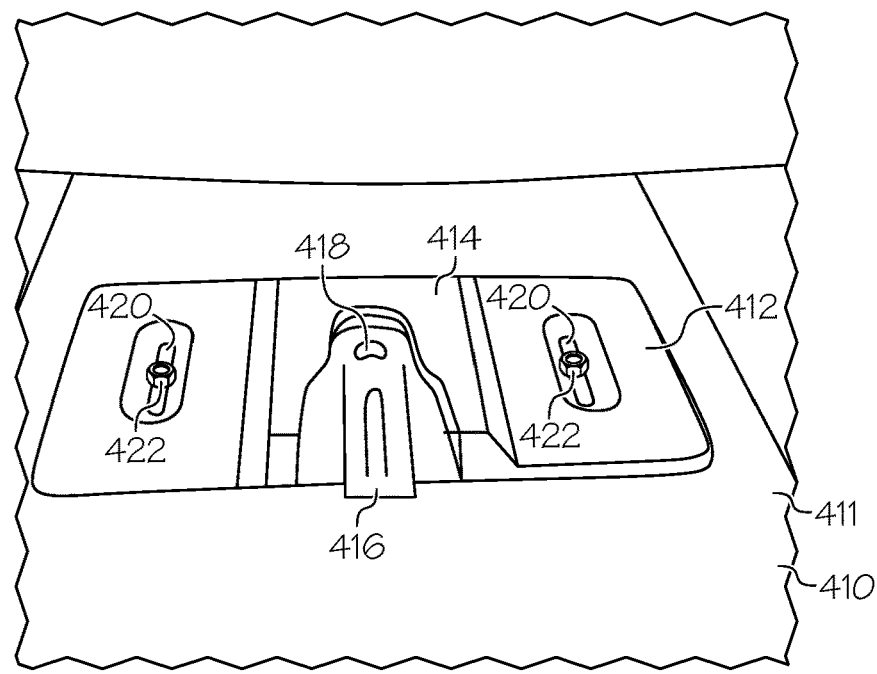
FIG. 4B depicts a perspective view of a mounting surface of a support platform of an imaging assembly including a support element for receiving the attachment element depicted in FIG. 4A, according to one or more embodiments described herein.

FIG. 4B depicts an upper surface 411 of a support platform 410 of a subject imaging assembly. An attachment element 412 is disposed on the upper surface 411 and is configured to engage with the recessed mounting member 404 described herein with respect to FIG. 4A. The attachment element 412 includes a protruding portion 414 that is shaped in a manner that corresponds to the recessed mounting member 404 disposed on the substrate 400. The attachment element 412 also includes a channel 416 adapted to receive the mounting peg 406 when the substrate 400 is attached to the support platform 410. The channel 416 includes an opening 418 adapted to receive the mounting protrusion 408 of the mounting peg 406 to prevent the substrate 400 from sliding once mounted on the support platform 410. The attachment element 412 includes a pair of slots 420 for fasteners 422 coupling the attachment element 412 to the support platform 410.

Figure 5A:
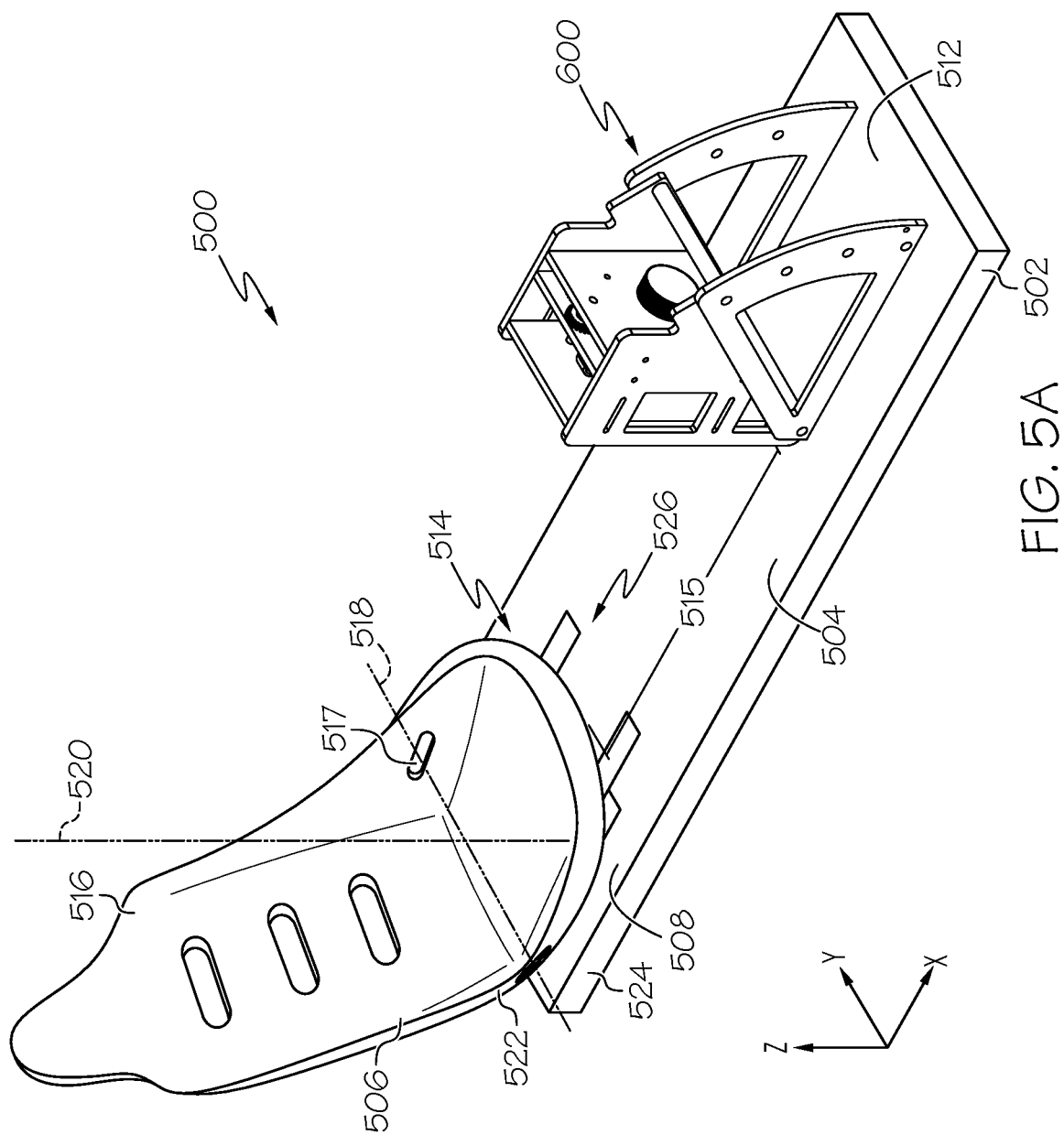
FIG. 5A depicts a perspective view of a weightbearing simulation assembly, according to one or more embodiments described herein.

Referring now to FIG. 5A, a perspective view of a weightbearing simulation assembly 500 is shown. In embodiments, the weightbearing simulation assembly 500 may be used in conjunction with a subject imaging assembly (e.g., the weightbearing simulation assembly 500 may serve as a replacement for the weightbearing simulation assembly 112 described herein with respect to FIGS. 1A, 1B, and 1C). The weightbearing simulation assembly 500 includes a substrate 502 having a mounting surface 504. The mounting surface 504 extends a first direction (e.g., the x-direction of the coordinate axes depicted in FIG. 5A). The first direction may correspond to a lengthwise axis of the substrate 502. In the depicted embodiment, the mounting surface 504 is a planar flat surface, but the mounting surface 504 may take various forms depending on the implementation. For example, in embodiments, the mounting surface 504 may include a plurality of portions extending in different directions or be curved.

The weightbearing simulation assembly 500 also includes a subject support 506 disposed on a first region 508 of the mounting surface 504. The subject support 506 is a seat having a first portion 514 and a second portion 516 extending at an angle (e.g., about 70 degrees to about 110 degrees) to the first portion 514. In embodiments, the first portion 514 and the second portion 516 are integrated into a single component such that the first portion 514 continuously extends into the second portion 516 via a curved transition region 522. In embodiments, the first portion 514 and the second portion 516 are separate components coupled to one another via a rotatable connection (not depicted) such that the angle between the second portion 516 and the first portion 514 may be adjusted to facilitate tilting a subject via the subject support 506 (e.g., to move an upper body of the subject away from a gantry of an imaging system). The subject support 506 is coupled to the mounting surface 504 via the first portion 514. In embodiments, the subject support 506 is not directly attached to the mounting surface 504 but to an alternative portion of the substrate 502. For example, the second portion 516 may be connected to the rear end 524 of the substrate 502 via a connection member (not depicted) extending from the second portion 516 to the rear end 524. In the depicted embodiment, the first portion 514 is coupled to the mounting surface 504 via a translation support mechanism 526 to facilitate adjusting a distance 515 between the subject support 506 and a pedal assembly 600 in the first direction. In embodiments, the translation support mechanism may be similar to the translation support mechanism 134 described herein with respect to FIGS. 1A, 1B, and 1C (e.g., include a pair of tracks, a rotatable support platform, a height adjustment element, or the like). As described herein, the translation support mechanism 526 may enable rotation of the subject support 506 about at least one axis of rotation. For example, via the translation support mechanism 526, the subject support 506 may be rotatably coupled to the mounting surface 504 to facilitate rotation of the subject support 506 about a first axis of rotation 520 that extends substantially perpendicular to the first direction (e.g., in the z-direction of the coordinate axes depicted in FIG. 5A).

Figure 5B:
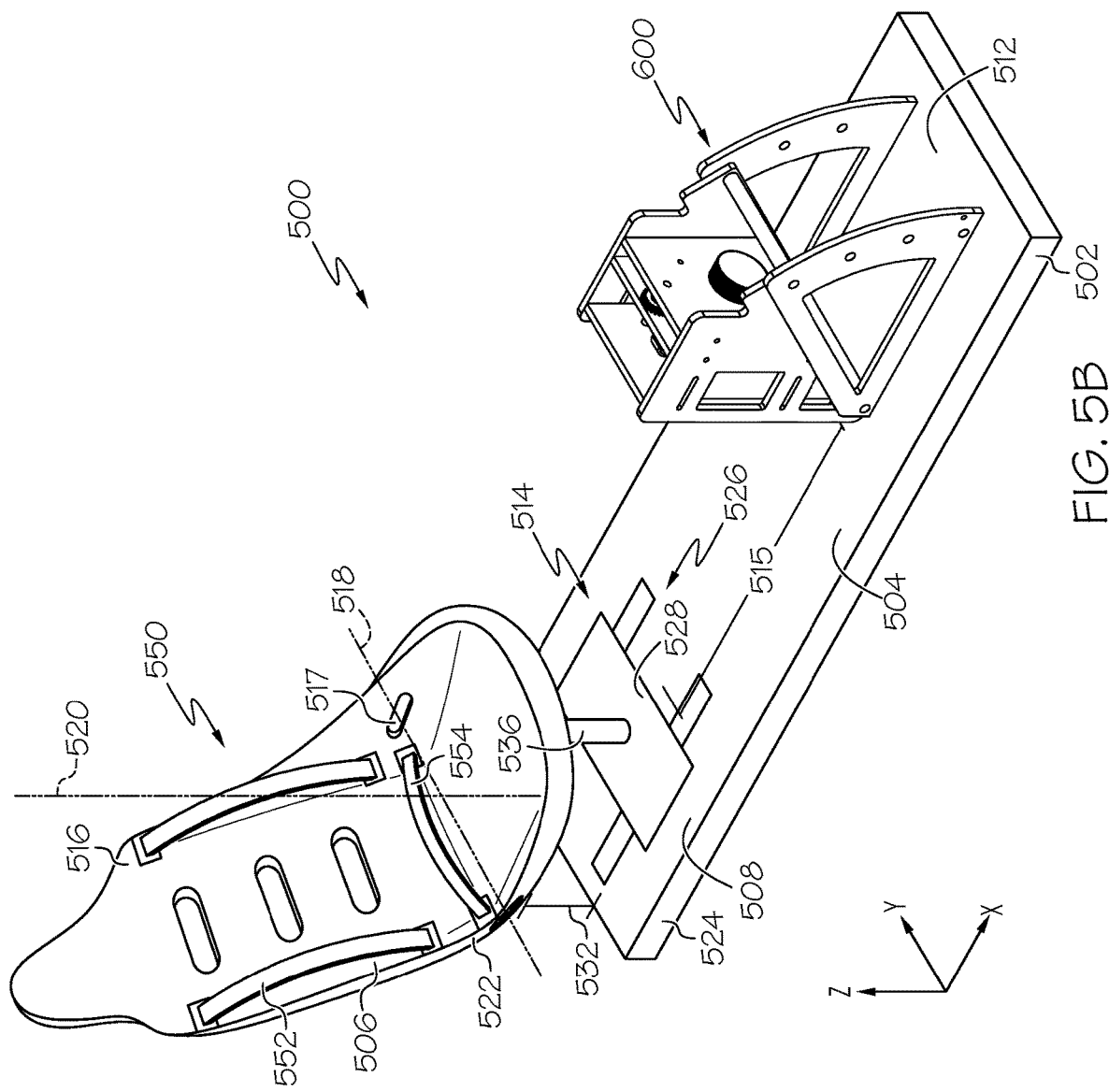
FIG. 5B depicts a perspective view of a weightbearing simulation assembly, according to one or more embodiments described herein.

Referring now to FIG. 5B, in embodiments, the translation support mechanism 526 includes a height adjusting element 536 such that the subject support 506 is separated from the mounting surface 504 by an adjustable distance 532 (e.g., in the z-direction depicted in FIG. 5B) to facilitate adjusting a height of a subject depending on the positioning of the subject's foot on the pedal assembly 600. As depicted, the height adjustment element 536 is disposed on a translating support platform 528 that is coupled to the translation support mechanism 526. The height adjustment element 536 may include any adjustable support capable of adjusting the relative positioning between the subject support 506 and the support surface 504. For example, in embodiments, the height adjusting element 536 includes a telescoping arm having a length that is adjustable in the z-direction so as to render the distance 532 adjustable. As described herein, a user may adjust the distance 532 depending on an orientation of the pedal assembly 600 (e.g., a relative angle between the compression direction 626 and the x-direction described herein with respect to FIGS. 6A-6F) to facilitate the subject supplying a compressive force to the pedal assembly 600 while maintaining proper positioning of the subject's foot.

The subject support 506 may include various features to assist a subject in supplying a load to the pedal assembly 600. For example, the subject support 506 includes handles 517 on the first portion 514 for the subject to grip while supplying compressive force to the pedal assembly 600. In embodiments, the subject support 506 includes a harness assembly 550. The harness assembly 550 includes shoulder straps 552 and a lower restraint 554. In embodiments, the harness assembly 550 only includes one of either the shoulder straps 552 or the lower restraint 554. The shoulder straps 552 and/or lower restraint 554 maintain the subject on the subject support 506 when the subject supplies a compressive force to the pedal assembly 600. As described herein, the pedal assembly 600 may be adjusted such that the direction in which the subject supplies compressive force may be adjusted. When the direction of compressive force is at angle to the first direction, application of the compressive force by the subject may force the subject upward (e.g., in the z-direction depicted in FIG. 5B). As such, the harness assembly 550 may prevent the subject from sliding on subject support 506 so that the subject remains stable for imaging. In embodiments, the handles 517 perform such a function in conjunction with the harness assembly 550. Via the handles 517, the subject may stabilize herself while supplying compressive force to the pedal assembly 600. The reclining of the subject support 506 (e.g., via rotation about the second axis of rotation 518 or adjusting the angle between the first portion 514 and the second portion 516) facilitates comfortably positioning the subject irrespective of a positioning of an accompanying imaging system.

The subject provides a compressive force to the pedal assembly 600 via a lower extremity (e.g., a foot). In response to the subject providing the compressive force, the pedal assembly 600 provides an adjustable amount of resistance to ensure that the subject supplies an adequate amount of compressive force to simulate a loadbearing condition for the subject. That is, the pedal assembly 600 effectively measures the compressive force supplied by the subject to ensure that the subject is supplying an adequate amount of compressive force for imaging. The pedal assembly 600 comprises an adjustable spring assembly (not depicted) that provides the adjustable amount of resistance. For example, in embodiments, the pedal assembly 600 may be adjusted to resist movement of the subject's lower extremity such that the subject is required to exert a compressive force that corresponds to approximately half of the weight of the subject in order to place the pedal assembly 600 into an imaging state. Such a resistance simulates a weightbearing condition for the subject. The structure of the pedal assembly 600 is described in more detail with respect to FIGS. 6A-6F. In embodiments, the weightbearing simulation assembly 500 includes radio-opaque shielding (not depicted) adapted to cover portions of the subject's lower extremity outside of the part being image to prevent radiation damage.

Figure 6A:
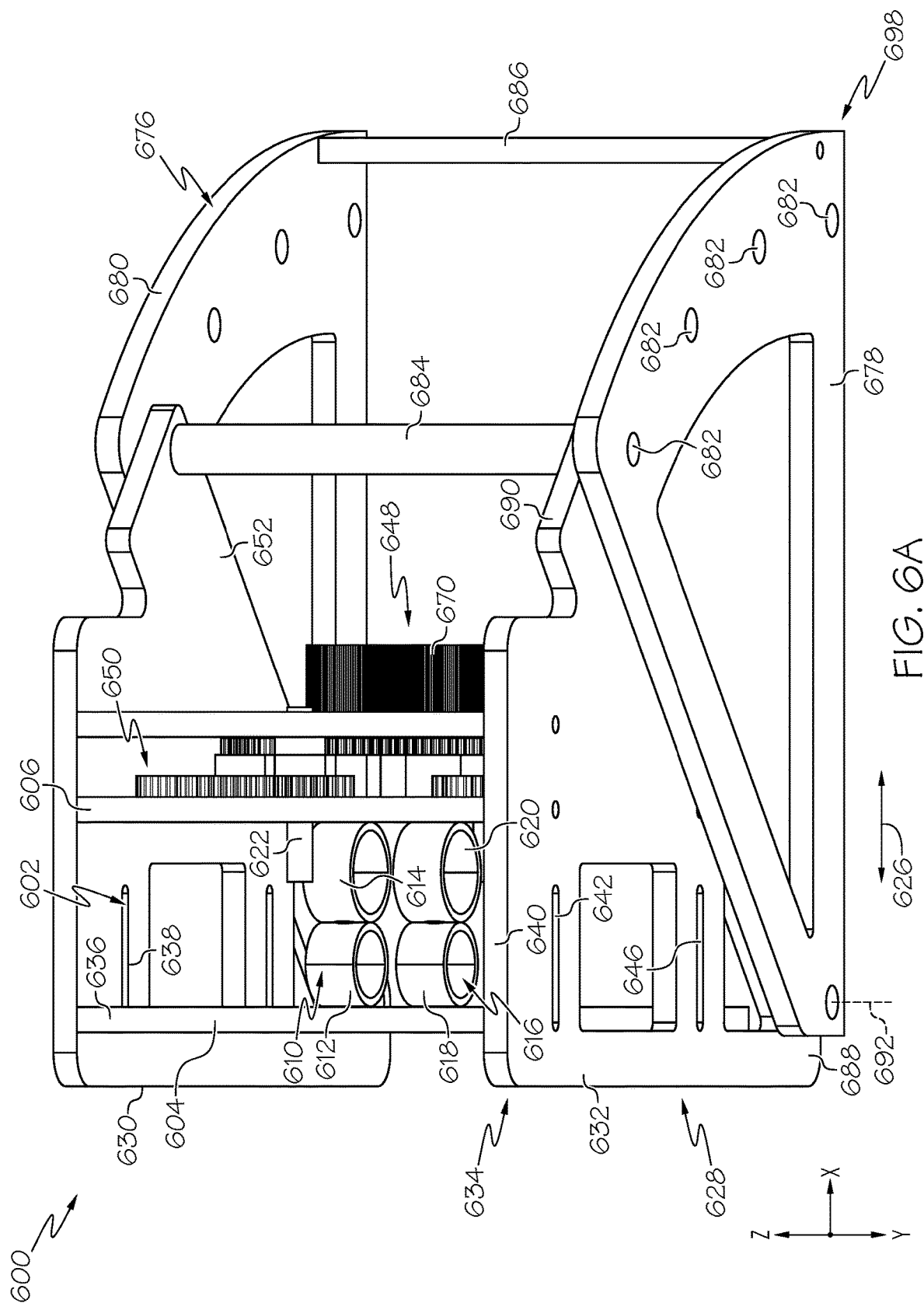
FIG. 6A depicts a perspective view of a pedal assembly, according to one or more embodiments described herein.
Figure 6B:
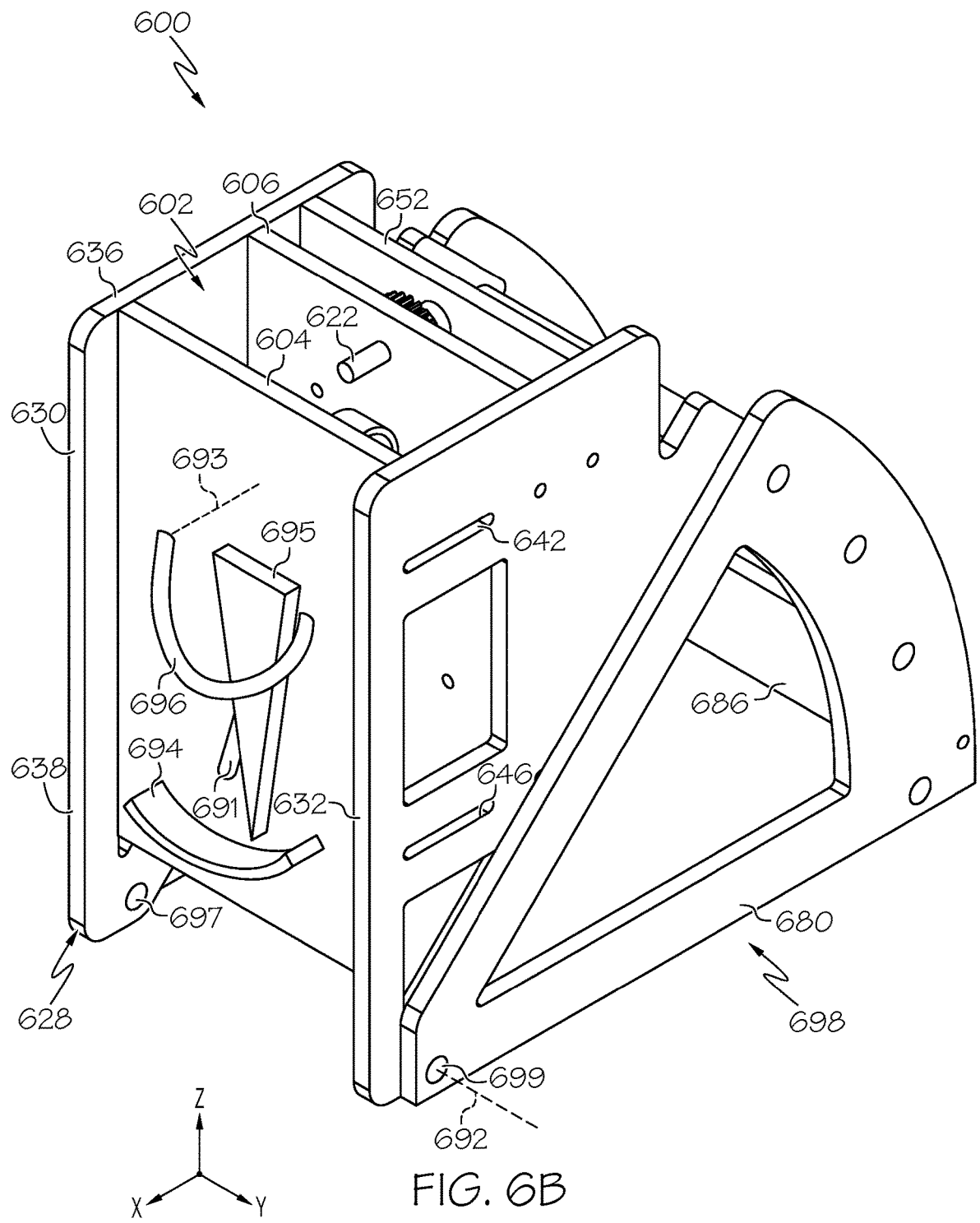
FIG. 6B depicts another perspective view of the pedal assembly shown in FIG. 6A, according to one or more embodiments described herein.

FIGS. 6A-6F depict various views of the pedal assembly 600. The pedal assembly 600 includes a spring assembly 602 supported via a pedal support assembly 628. The spring assembly 602 includes a contact plate 604, compression plate 606, and a first spring member 610 extending between the contact plate 604 and the compression plate 606. The contact plate 604 faces the subject support 506 when the pedal assembly 600 is disposed on the mounting surface 504 of the substrate 502. A subject being imaged generally places a bottom surface of their foot in contact with the contact plate 604 to supply a load to the contact plate 604. As depicted in FIG. 6B, the contact plate 604 may include a heel cup 694 disposed thereon to facilitate the subject positioning the foot properly with respect to the first spring member 610 to ensure uniform application of compressive force to the foot via the spring assembly 602. The contact plate 604 may also include an adjustable strap 696 for securing the subject's forefoot or midfoot to the contact plate 604 so that the subject's foot remains stable during imaging while the compressive force is supplied to the subject's foot. In embodiments, the heel cup 694 and the adjustable strap 696 are rotatably disposed on the contact plate 604 (e.g., the heel cup 694 and the adjustable strap 696 may be part of a foot holding assembly that is rotatably mounted on the contact plate). In embodiments, the foot holding assembly may be rotated with respect to a surface normal 693 of the contact plate 604 to provide alternative imaging angles. It should be understood that alternative embodiments for securing the foot of the subject to the contact plate 604 are envisioned. For example, in certain implementations, the contact plate 604 includes an attachment element for an item (e.g., a sock, shoe, etc.) worn by the subject. In an example, the attachment element may include Velcro® or the like that is also included on the item worn by the subject.

Referring to FIG. 6B, the contact plate 604 may also include at least one rotation block 695 disposed thereon. In embodiments, the rotation block 695 is a triangular wedge adapted to be inserted under a side of the subject's foot. In embodiments, the rotation block 695 is rotatable about an axis (e.g., extending parallel to the surface normal 693) to adjust an orientation of the subject's foot when the foot is aligned along the rotation block 695. The rotation block 695 may be attached to the contact plate 604 by any suitable means. For example, in embodiments, the rotation block 695 is attached to the contact plate 604 via a removable connection (e.g., Velcro®) to facilitate changing out the rotation blocks 695. As depicted, in embodiments, the rotation block 695 is as attached to the contract plate via an adjustable element 691 (e.g., a track, a Velcro® strip, etc.) to render the positioning of the rotation block 695 adjustable on the contact plate 604. While the contact plate 604 is depicted as only incorporating a single rotation block 695, it should be appreciated that the contact plate 604 may include any number of rotation blocks arranged in a variety of different configurations.

Figure 6C:
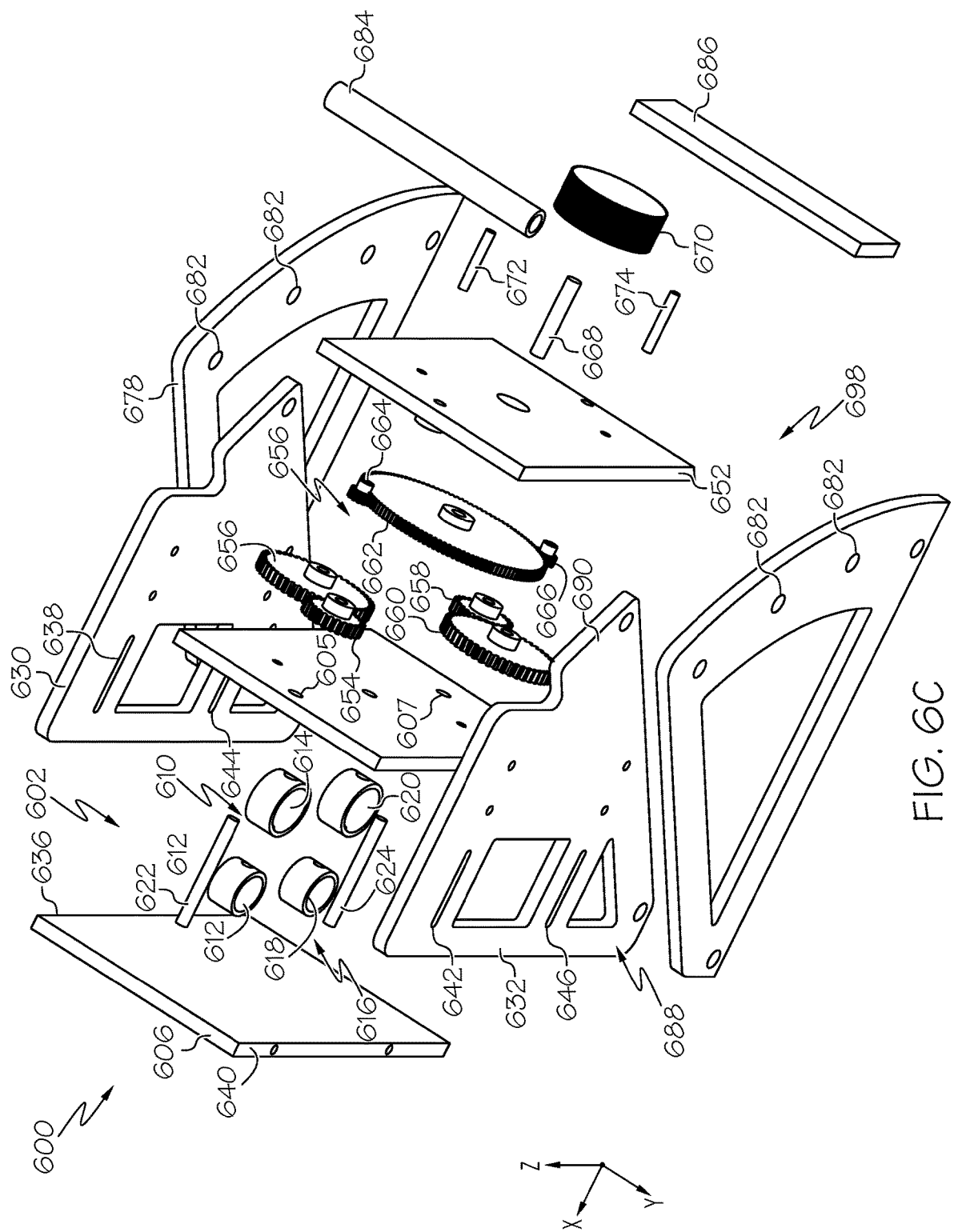
FIG. 6C depicts an exploded view of the pedal assembly shown in FIG. 6A, according to one or more embodiments described herein.

As depicted in FIGS. 6A and 6C, the spring assembly 602 includes the first spring member 610 and a second spring member 616. The first and second spring members 610 and 616 are attached to the contact plate 604 and extend in a compression direction 626 between the contact plate 604 and the compression plate 606. The first spring member 610 includes a first spring 612 and a second spring 614, while the second spring member 616 includes a third spring 618 and a fourth spring 620. In embodiments, the first spring 612 and the second spring 614 are cylindrical polymer spring members having axes extending parallel to one another and perpendicular to the compression direction 626. In embodiments, the first spring 612 and second spring 614 are selected such that, in combination, the first spring 612 and the second spring 614 provide an amount of force per unit of compression to enable provision of resistance to simulate a weightbearing condition for the subject. The second spring 614 is coupled to the compression plate 606 via a fastener (not depicted) extending through the second spring 614 and the compression plate 606. The first spring 612 is coupled to the contact plate 604 via a fastener (not depicted) extending through the first spring 612 into the contact plate 604. The first spring 612 is attached to the second spring 614 via a fastener (not depicted) contacting both the first and second springs 612 and 614. The third and fourth springs 618 and 620 of the second spring member 616 may be structured similarly to the first and second springs 612 and 614 of the first spring member 610.

The first and second spring members 610 and 616 are arranged to resist movement of the contact plate 604 in the compression direction 626 responsive to the subject supplying a compressive force to the contact plate 604. The compression direction 626 extends perpendicular to the contact plate 604 and the compression plate 606. Such an orientation of the compression direction 626 with respect to the compression plate 606 and contact plate 604 simplifies calibration of the spring assembly 602 by applying a force to the subject's foot that corresponds to a flat surface under gravity, through alternative relative orientations of the compression direction 626 and the contact plate 604 are possible to simulate different situations (e.g., an inclined load).

The first and second spring members 610 and 616 are distributed to provide resistance of motion to an entirety of the subject's foot that the subject is required to supply the compressive force to the pedal assembly using substantially the entirety of the subject's foot. For example, in embodiments, the first spring member 610 is positioned to resist movement of a first portion of the subject's foot (e.g., the metatarsals) and the second spring member 616 is positioned to resist movement of a second portion of the subject's foot (e.g., the calcaneus). This way, the spring assembly 602 ensures that the subject supplies approximately 50% of the compressive force using the metatarsals and approximately 50% of the compressive force using the heel. Such a configuration prevents the subject from applying their weight using only a portion of her foot and ensures that the pedal assembly 600 simulates a true weightbearing condition for the subject. The first and second spring members 610 and 616 may each supply the same resistance of motion of the contact plate 604 so as to simulate a uniform load being supplied across an entirety of the subject's foot. In embodiments, the first and second spring members 610 and 616 resist motion of the contact plate 604 in differing amounts to provide a customized load distribution to the subject's foot.

The number of spring members included in the spring assembly 602 may vary. For example, certain embodiments may include only a single spring member (e.g., extending between central portions of the contact plate 604 and the compression plate 606). Moreover, the first and second spring members 610 and 616 may possess various alternative structures than those depicted. For example, in embodiments, the first and second spring members 610 and 616 may each only include a single spring. In such embodiments, the single spring of the first and second spring members 610 and 616 may take the form of the first spring 612 described above (e.g., a cylindrical polymer spring member having an axis oriented perpendicular to the compression direction 626). Alternatively, the single spring may take a different form (e.g., a metal leaf spring, a coil-shaped spring member, an elastic material, etc.). It should be appreciated that the spring assembly 602 may include any number of springs in any form consistent with the present disclosure.

In embodiments, the spring assembly 602 may include a sensor (not depicted) for measuring the compressive force supplied by the subject. For example, in embodiments, the spring assembly 602 comprises a pressure sensor adapted to measure the compressive force on the contact plate 604 provided by the subject. The pressure sensor may include a piezoelectric pressure sensor, an electromagnetic pressure sensor, an optical pressure sensor, a capacitive pressure sensor, or any other available pressure sensor adaptable to measure the compressive force supplied via the foot of the subject. In embodiments, the spring assembly 602 may include a plurality of pressure sensors to measure the pressure supplied via the subject at various portions of the contact plate 604 (e.g., corresponding to the portions of the contact plate 604 overlapping the first and second spring members 610 and 616). Alternatively or additionally, the spring assembly 602 may include a force sensor configured to measure a total force applied to the contact plate 604. In certain embodiments where the spring assembly 602 incorporates such a sensor, the spring assembly 602 may not include the first and second spring members 610 and 616 and the pedal assembly 600 may provide an indication via the sensor (e.g., via a light or sound generator coupled to the sensor) of when the subject has supplied a desired amount and distribution of compressive force to the contact plate 604 for imaging.

The spring assembly 602 also includes a first motion limiter 622 and a second motion limiter 624 coupled to the compression plate 606 via an adjustable assembly 650. As depicted in FIG. 6E, when the spring assembly 602 is in an unloaded state (e.g., when the subject does not supply a compressive to the contact plate 604) the contact plate 604 and the compression plate 606 are separated by a first distance 153 in the compression direction 626 and the first and second spring members 610 and 616 contact both the contact plate 604 and the compression plate 606. In embodiments, the first and second spring members 610 and 616 may not contact the contact plate 604 when the spring assembly 602 is in the unloaded state (e.g., the first and second spring members 610 and 616 may only be connected to the compression plate 206 in such embodiments). When the spring assembly 602 is in the unloaded state, ends 623 and 635 of the first and second motion limiters 622 and 624 are disposed between the contact plate 604 and the compression plate 606. The positioning of the ends 623 and 625 of the first and second motion limiters 622 and 624 determines a range of motion of the contact plate 604 relative to the compression plate 606.

Figure 6D:
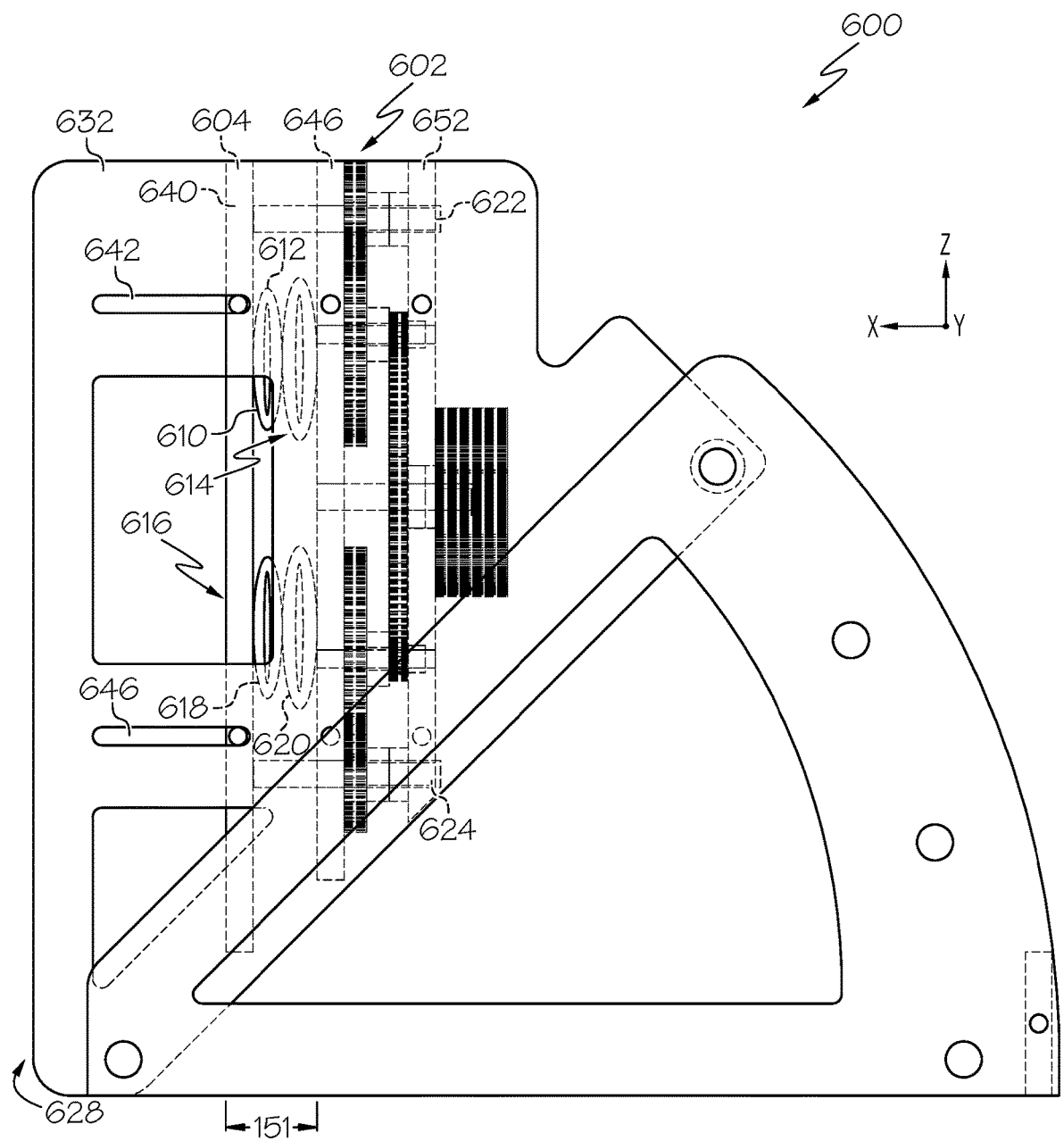
FIG. 6D depicts a perspective view of the pedal assembly shown in FIG. 6A in a loaded state, according to one or more embodiments described herein.
Figure 6E:
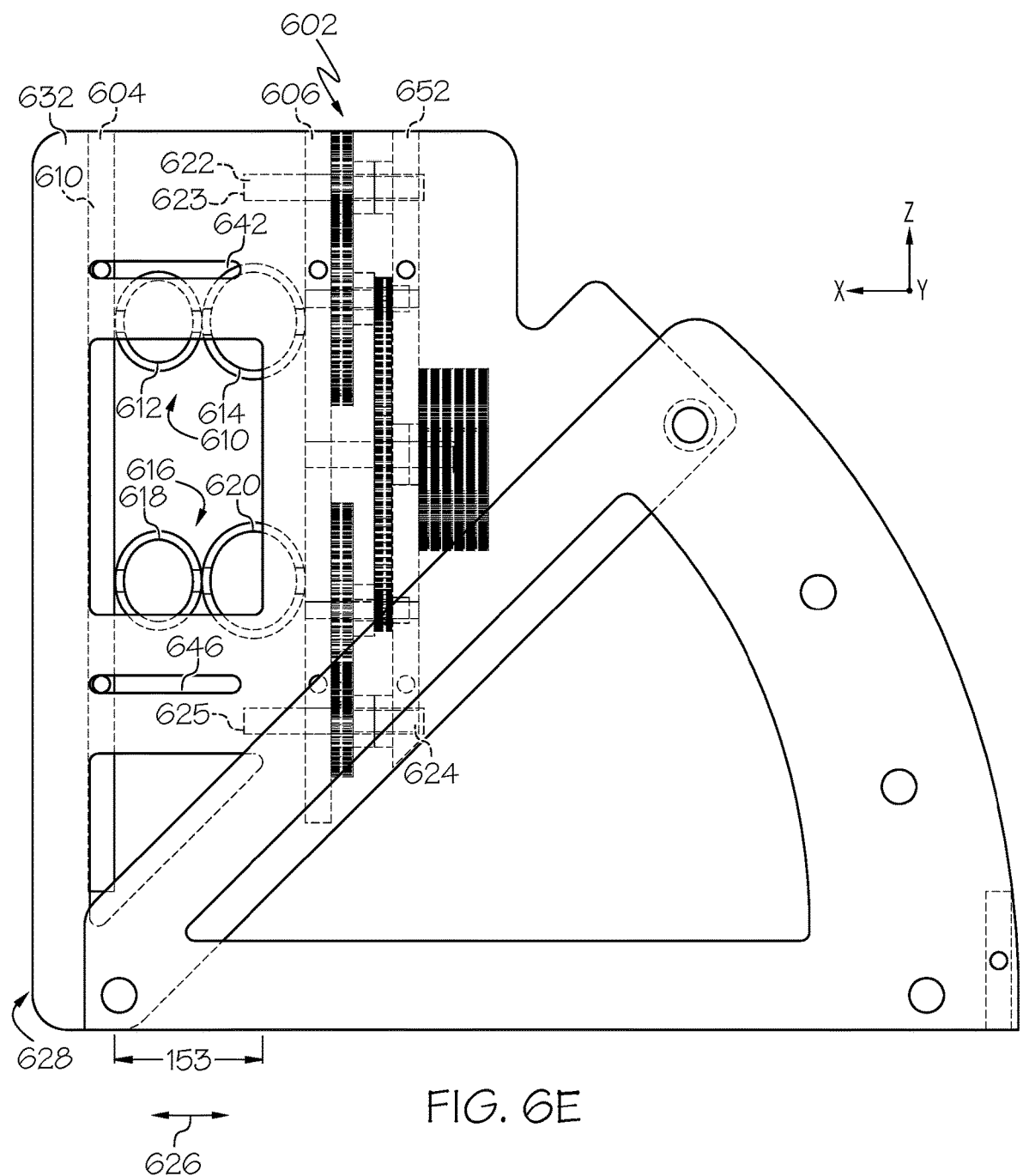
FIG. 6E depicts a perspective view of the pedal assembly shown in FIG. 6A in an unloaded state, according to one or more embodiments described herein.

As depicted in FIG. 6D, when the spring assembly 602 is in a loaded state (e.g., when a subject supplies compressive force to sufficiently compress the first and second spring members 610 and 616) the contact plate 604 contacts the ends 623 and 625 of the first and second motion limiters 622 and 624. The first and second motion limiters 622 and 624 may be secured within the pedal support assembly 628 such that first and second motion limiters 622 and 624 are stationary relative to the compression plate 606 and the positioning of the ends 623 and 625 of the motion limiters 622 and 624 determines a range of motion of the contact plate 604. When the spring assembly 602 is in the loaded state, the contact plate 604 and the compression plate 606 are separated by a second distance 151 in the compression direction 626 and the first and second spring members 610 and 616 resist movement of contact plate 604 in an amount that is proportional to the amount of displacement of the contact plate 604 caused by the subject. In other words, the difference between the first distance 153 between the contact plate 604 and the compression plate 606 when the spring assembly 602 is in an unloaded state and the second distance 151 between the contact plate 604 and the compression plate 606 when the spring assembly is in a loaded state determines the resistance to the subject's foot applied via the spring assembly 602.

In embodiments, the positioning of the first motion limiter 622 and the second motion limiter 624 relative to the compression plate 606 (and therefore the amount of compressive force supplied via the spring assembly 602 when the spring assembly 602 is placed in the loaded state) is adjustable via the adjustable assembly 650. As shown in FIGS. 6A and 6C, the adjustable assembly 650 is a gear assembly comprising a first driving gear 654 and a second driving gear 658 that are attached to a fixed plate 652 via the first and second motion limiters 622 and 624. In embodiments the first and second motion limiters 622 and 624 include threaded rods extending through the contact plate 604, the first and second driving gears 654 and 658, respectively, and the fixed plate 652. The first and second motion limiters 622 and 624 may extend through threaded openings 605 and 607 in the contact plate 604 such that rotation of the driving gears 654 and 658 adjusts the positioning of the first and second motion limiters 622 and 624 in the compression direction 626. The first driving gear 654 is in engagement with a first lower gear 656 that is coupled to the fixed plate 652 via a shaft 672. The second driving gear 658 in engagement with a second lower gear 660 that is coupled to the fixed plate 652 via a shaft 674. The first lower gear 656 is attached to a first upper gear 664 that also attached to the fixed plate 652 via the shaft 672. The second lower gear 660 is attached to a second upper gear 666 that is also attached to the fixed plate via the shaft 674. The first and second upper gears 664 and 666 are both in engagement with a central gear 662 that is attached to an adjustment knob 670 via a shaft 668 extending through the fixed plate 652. As such, rotation of the adjustment knob 670 by a user causes rotation of the central gear 662, which in turn causes rotation of the upper and lower gears 656, 660, 664, and 666, and rotation of the first and second lower gears 656 and 660 in turn causes rotation of the first and second driving gears 654 and 658 to rotate the first and second motion limiters 622 and 624 and adjust the positioning of the first and second motion limiters 622 and 624 in unison to adjust the compressive force supplied via the spring assembly 602 when the spring assembly is placed in the loaded state depicted in FIG. 6D. The adjustable assembly 650 ensures alignment between the first and second motion limiters 622 and 624 such that a uniform compressive force is supplied to the contact plate 604 via the spring assembly 602. Moreover, the multi-gear coupling of the adjustable assembly 650 facilitates fine tuning of the positioning of the first and second motion limiters 622 and 624 so that the compressive force may be accurately tuned. Alternative embodiments of the adjustable assembly 650 are envisioned. For example, in embodiments, the adjustable assembly 650 may include a different gear assembly having more or fewer elements than the adjustable assembly depicted in FIGS. 6A-6C. An example of an alternative gear assembly is described herein with respect to FIG. 8. In embodiments, the first and second motion limiters 622 and 624 are independently adjustable. For example, each of the first and second motion limiters 622 and 624 may each be attached an independently adjustable gear assembly having an independent adjustment knob. In embodiments, the adjustable assembly 650 may include an actuator configured to electrically adjust the adjustment knob 670 (or any other element that can be manipulated) in response to a user input. In embodiments, the adjustable assembly 650 or spring assembly 602 may include a sensor, detector, or the like, and may provide an output based on a compressive force supplied by the subject (e.g., measuring an amount of compressive force). In embodiments, the adjustable assembly 650 may include a translating assembly coupled to the contact plate 604.

The pedal support assembly 628 includes a first side plate 630 and a second side plate 632 that define a channel 634 in which the spring assembly 602 is disposed. The first side plate 630 includes slots 638 and 644 for receiving fasteners (not depicted) that extend into a first side edge 636 of the contact plate 604. The second slide plate 632 includes slots 642 and 646 for receiving fasteners (not depicted) that extend into a second side edge 640 of the contact plate 604. The slots 638, 642, 644, and 646 extend in the compression direction 626 to facilitate movement of the contact plate 604 relative to the compression plate 606. In embodiments, the compression plate 606 and the fixed plate 652 are also attached to the first and second side plates 630 and 632 via fasteners (not depicted) extending through the first and second side plates 630 such that the fixed plate 652 and the compression plate 606 are fixed in relation to the contact plate 604. It should be appreciated that a number of alternative structures for the pedal support assembly 628 are envisioned. For example, in embodiments, the pedal support assembly 628 includes a support carriage (not depicted) that directly contacts the substrate 502 along a contact distance for directly attaching the pedal support assembly 628 to the substrate 502. The support carriage may include side walls having structures similar to the first and second side plates 630 and 632 to facilitate supporting the spring assembly 602.

As depicted in FIG. 6A, the pedal support assembly 628 is oriented such that the contact plate 604 and the compression plate 606 extend largely in the y-z plane defined by the coordinate axes of FIG. 6A. In such an orientation, the contact plate 604 and the compression plate 606 extend substantially perpendicular to the mounting surface 504 of the substrate 502 depicted in FIG. 5A. Such an orientation may be useful for imaging the subject's ankle. However, it may be also be useful to image the subject's foot in alternative orientations. For example, it may be useful to adjust the orientation of the spring assembly 602 such that the contact plate 604 and the compression plate 606 extend at an angle relative to the z-direction of the coordinate axes of FIG. 6A of about 30 degrees or about 60 degrees or any angle between and including zero degrees and 60 degrees to facilitate imaging various portions (e.g., the angle, forefoot, and hinfoot) of the subject's foot. In this regard, the pedal support assembly 628 is supported by an adjustable support element 698 (see FIG. 6C) having a plurality of support positions 682. In embodiments, the user may select from among the plurality of support positions 682 to change the orientation of the spring assembly 602 (e.g., to adjust a relative angle between the compression direction 626 and a direction of extension of the substrate 502).

As depicted in FIG. 6C, the adjustable support element 698 includes a first propping plate 678 and a second propping plate 680 coupled to one another via the spring assembly 602 and a rear brace 686 extending between the first and second propping plates 678 and 680. In embodiments, the first and second propping plates 678 and 680 are directly attached to the mounting surface 504 of the substrate 502. As depicted in FIG. 6B, the adjustable support element 698 includes openings 699 at a pivot axis 692 of the pedal support assembly 628. In embodiments, a connection rod (not depicted) extends through the openings 699 at the pivot axis 692 and through corresponding openings 697 in a first portion 688 of the pedal support assembly 628 (see FIG. 6E) to rotatably couple the first portion 688 to the adjustable support element 698. A second portion 690 of the pedal support assembly 628 is coupled to the adjustable support element 698 at one of the support positions 682 via a propping rod 684. In embodiments, a user may remove the propping rod 684 from a first one of the support positions 682, realign the pedal support assembly 628 with respect to the adjustable support element 698 such that the second portion 690 is aligned with respect to a second one of the support positions 682, and re-insert the propping rod 684 through the second portion 690 to adjust the orientation of the spring assembly 602. In embodiments, the plurality of support positions 682 extend in equally spaced angular intervals along an arc. In the example depicted, by selecting from among the plurality of support positions 682, a user may adjust the orientation of the compression direction 626 in angular (e.g., about 30 degree) increments with respect to the z-direction of the coordinate axes of FIG. 6B (e.g., about 0 degrees, about 30 degrees, about 60 degrees, or the like).

Figure 6F:
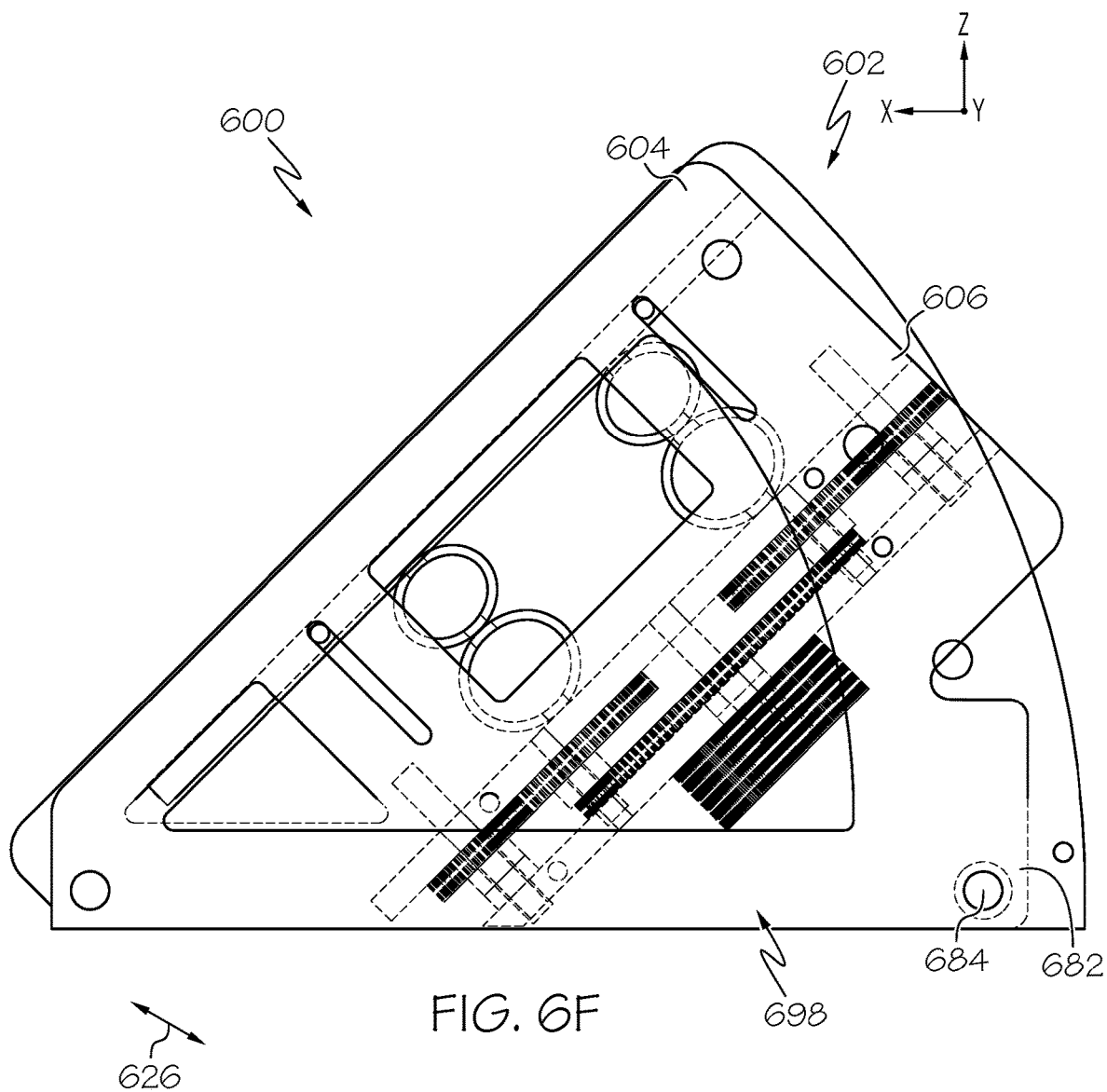
FIG. 6F depicts a perspective view of the pedal assembly shown in FIG. 6A having a compression direction in an alternative orientation, according to one or more embodiments described herein.

FIG. 6F depicts a perspective view of the pedal assembly 600 where the propping rod 684 is inserted into a support position of the plurality of support positions 682 of the adjustable support element 698 that is most proximate to the mounting surface 504 of the weightbearing simulation assembly 500. As depicted, in such a configuration, the compression direction 626 is angled approximately 45 degrees relative to the first direction (e.g., the x-direction depicted in FIG. 6F) to facilitate imaging a hindfoot of the subject. In embodiments, when the pedal assembly 600 is oriented in the manner depicted in FIG. 6F, other adjustments to the weightbearing simulation assembly 500 are made to facilitate imaging. For example, referring to FIG. 5B, the height adjusting element 536 may be adjusted such that the adjustable distance 532 is greater when the pedal assembly 600 is oriented as depicted in FIG. 6F than when the pedal assembly 600 is oriented as depicted in FIGS. 6A-6B. In embodiments, when one of the plurality of support positions 682 of the adjustable support element 698 is selected (e.g., to select a particular orientation of the compression direction 626), the adjustable distance 532 is adjusted to a particular value based on the selected orientation of the compression direction 626 in accordance with a predetermined orientation-height scheme.

Alternatives to adjustable support element 698 are envisioned. For example, in embodiments, the pedal support assembly 628 is disposed directly on the substrate 502 and not supported by the adjustable support element 698, which may result in an orientation of the pedal assembly 600 where the compression direction 626 extends at a non-zero angle (e.g., about 60 degrees) from the z-direction of the coordinate axes of FIGS. 6A and 6B. In such embodiments, the entirety of the pedal support assembly 628 may be disposed on a rotatable platform to facilitate angular adjustment of the spring assembly 602. Alternatively, an alternative adjustable support element may be used. An example of such an alternative support element is described herein with respect to FIG. 9.

Figure 7:
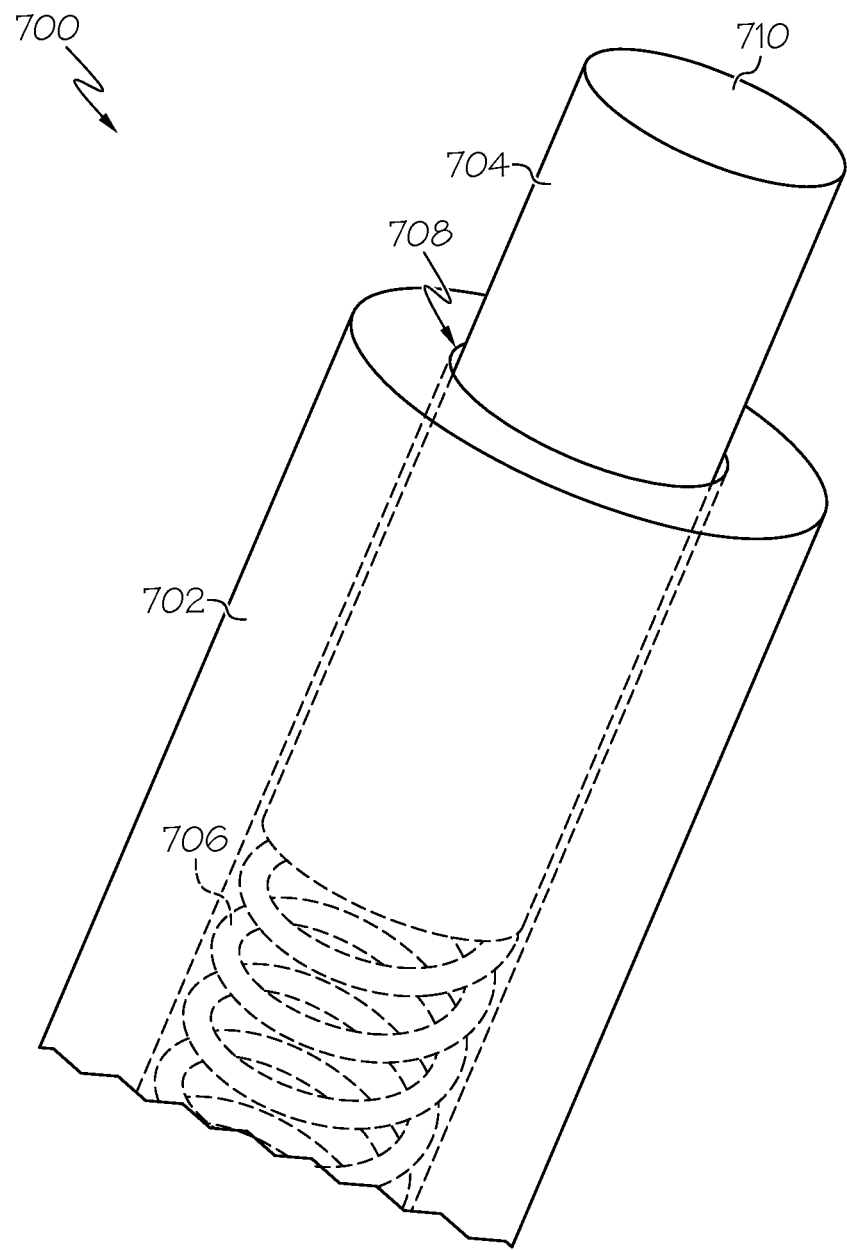
FIG. 7 depicts a perspective view of a motion limiter for a pedal assembly, according to one or more embodiments described herein.

Referring now to FIG. 7, a perspective view of a motion limiter 700 is depicted. In embodiments, the motion limiter 700 may be used in place of at least one of the first and second motion limiters 622 and 624 depicted in FIGS. 6A-6F. The motion limiter 700 includes a threaded rod 702 having a plunger 704 disposed in an opening 708 formed within the threaded rod 702. A spring element 706 supports the plunger 704 within the opening 708. In embodiments, the spring element 706 is attached to a compression plate (e.g., the compression plate 606) of a spring assembly (e.g., the spring assembly 602). For example, in embodiments, the spring assembly 602 includes two of the motion limiters 700 in place of the first and second motion limiters 622 and 624. The plunger 704 of each motion limiter 700 extends from the compression plate 606 and is supported by the spring element 706 such that the end 710 of the plunger 704 extends outward from the threaded rod 702. In operation, once the subject supplies the load to the contact plate 604 and the contact plate 604 contacts the motion limiter 700, the contact plate 604 initially compresses the spring element 706 via contacting the end 710 of the plunger 704. The spring element 706 beneficially dampens the impact between the contact plate 604 and the motion limiter 700.

Figure 8:
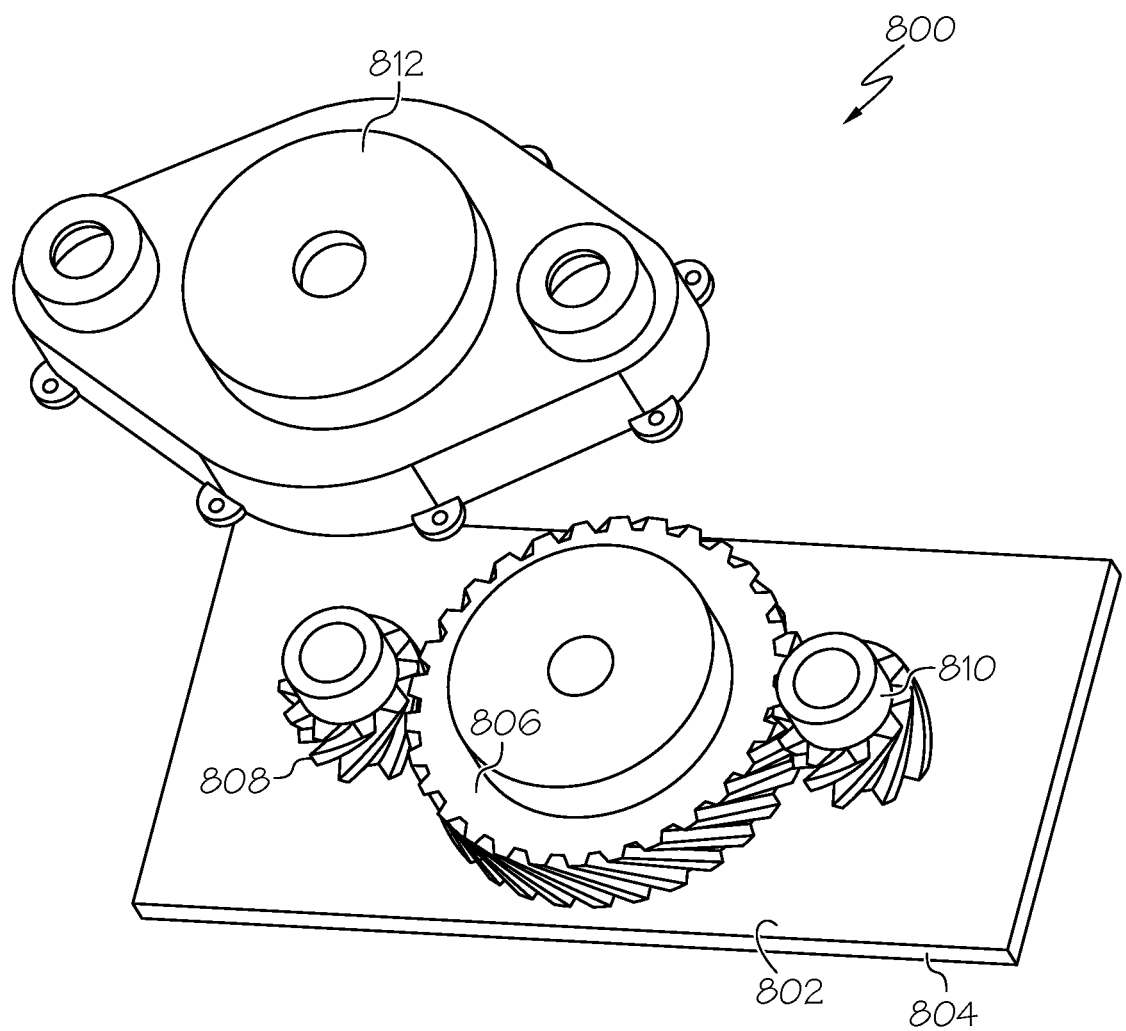
FIG. 8 depicts a perspective view of a gear assembly for a pedal assembly, according to one or more embodiments described herein.

Referring now to FIG. 8, a perspective view of a gear assembly 800 for a pedal assembly of a weightbearing simulation assembly is depicted. For example, in embodiments, the gear assembly 800 may be used in place of the adjustable assembly 650 described herein with respect to FIGS. 6A-6F. The gear assembly 800 includes a first driving gear 808 and a second driving gear 810. The first and second driving gears 808 and 810 may be coupled motion limiters of the spring assembly (not depicted) extending through a compression plate 804. The first and second driving gears 808 and 810 are each mechanically engaged to a central gear 806 such that rotation of the central gear 806 causes a rotation of the motion limiters coupled to the first and second driving gears 808 and 810 and an adjustment in the positioning of the motion limiters. A gear cover 812 (e.g., in place of the fixed plate 652 described with respect to FIGS. 6A-6F) covers the adjustable gear assembly 800 to protect the gear assembly 800 from dust or other debris to ensure long-term operation. The gear assembly 800 has fewer components than the adjustable assembly 650 described with respect to FIGS. 6A-6F, but does not enable as fine of adjustment of the compressive force supplied by spring assembly.

Figure 9:
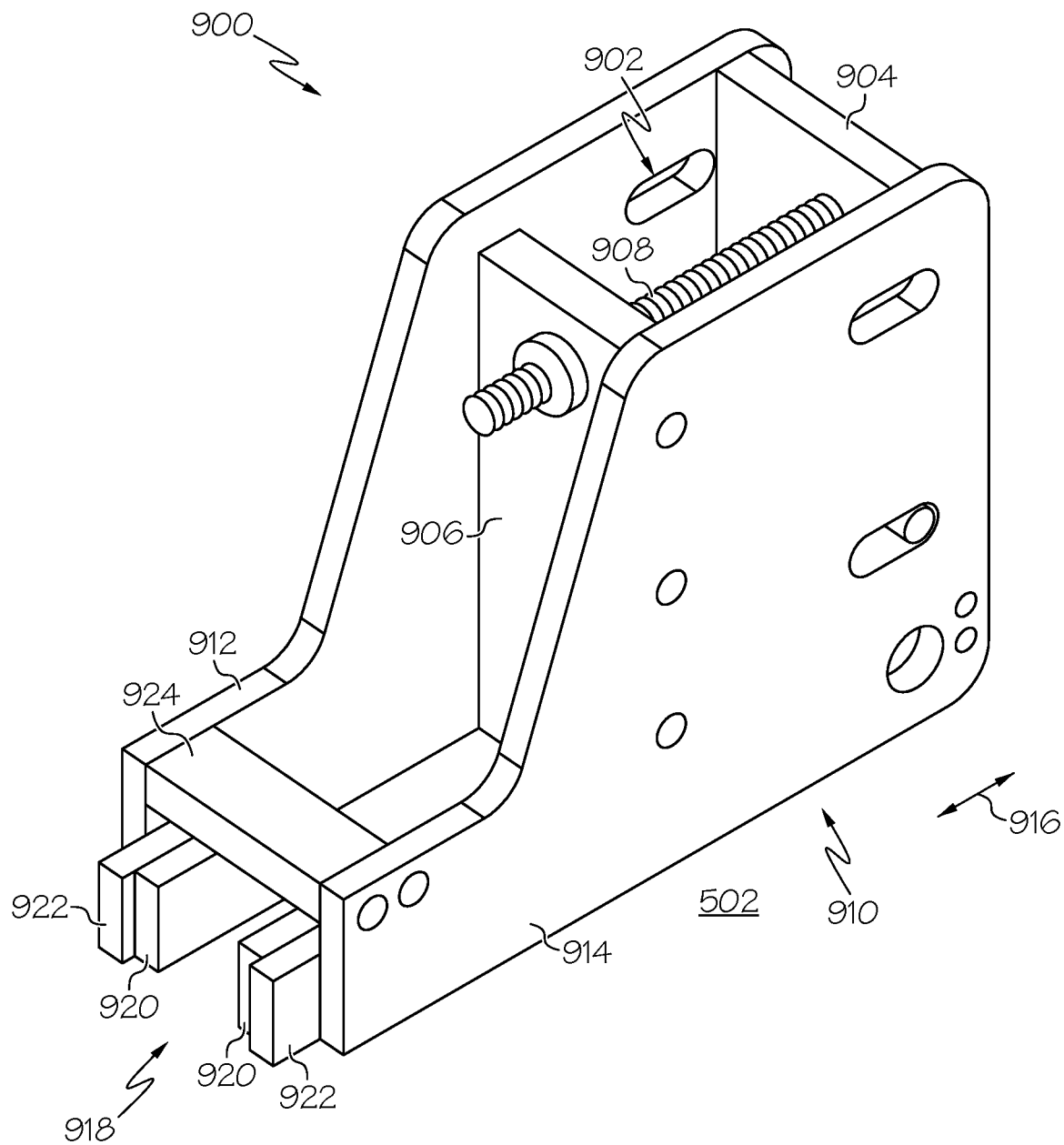
FIG. 9 depicts a perspective view of a pedal assembly, according to one or more embodiments described herein.

Referring now to FIG. 9, another pedal assembly 900 is depicted. The pedal assembly 900 may be used in place of the pedal assembly 600 described herein with respect to FIGS. 6A-6F. The pedal assembly includes a spring assembly 902 having a contact plate 904 and a compression plate 906 separated by a first motion limiter 908 and a second motion limiter (not depicted). In embodiments, the first motion limiter 908 is coupled to the compression plate 906 via the gear assembly 800 (e.g., the first driving gear 808) described with respect to FIG. 8. The spring assembly 902 includes a spring member (not depicted) extending in a compression direction 916 between the contact plate 904 and the compression plate 906.

The pedal assembly 900 includes a pedal support assembly 910 that includes a first side plate 912 and a second side plate 914. The first and second side plates 912 and 914 are shaped to be disposed directly on the mounting surface 504 of the substrate 502 of the weightbearing simulation assembly 500. As depicted, the first and second side plates 912 and 914 are oriented such that, when disposed on the mounting surface 504, the compression direction 916 extends at an angle to the mounting surface 504. To adjust the relative angle between the compression direction 916 and the mounting surface 504, the pedal support assembly 910 includes an adjustable support element 918. The adjustable support element 918 includes a first pair of elevation blocks 920 and a second pair of elevation blocks 922. The first pair of elevation blocks 920 have a smaller dimension (e.g., length) than the second pair of elevation blocks 922. In embodiments, both the first and second pairs of elevation blocks 920 and 922 are rotatable with respect to the pedal support assembly 910. In the depicted configuration, the first and second pairs of elevation blocks 920 and 922 are disposed on the mounting surface 504 and do not support the pedal support assembly 910. In embodiments, a user may rotate either first pair of elevation blocks 920 or the second pair of elevation blocks 922 such that either the first pair of elevation blocks 920 or the second pair of elevation blocks 922 supports a rear brace 924 of the pedal support assembly 910 to adjust the relative angle between the compression direction 916 and the mounting surface 504.

Figure 10:
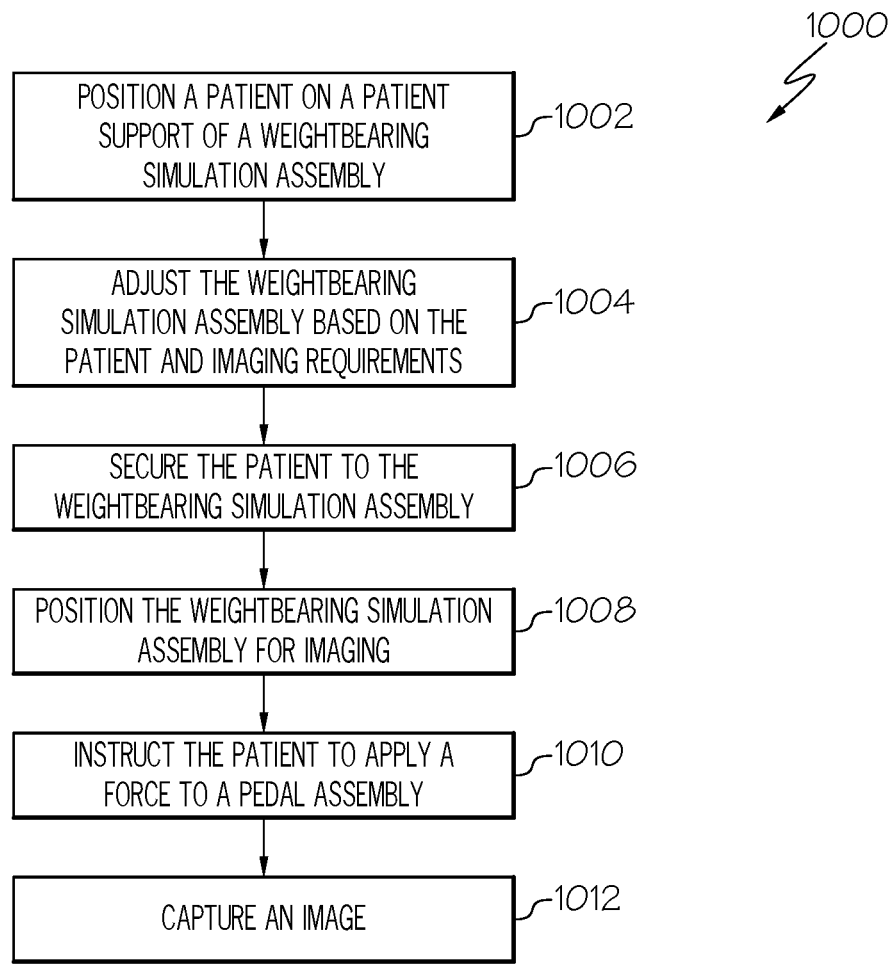
FIG. 10 depicts a flow diagram of a method for capturing an image of a subject using a weightbearing simulation assembly, according to one or more embodiments described herein.

Referring now to FIG. 10 a flow diagram of an illustrative method 1000 for capturing a load-bearing image of a lower extremity of a subject is shown. The method 1000 may be performed via the weightbearing simulation assembly 500 described herein used in combination with a subject imaging assembly. For example, in embodiments, the weightbearing simulation assembly 500 may disposed on the support platform 102 of the subject imaging assembly 100 described herein with respect to FIGS. 1A-1C to capture a load-bearing image of the lower extremity of the subject via performance of the method 1000. In embodiments, the weightbearing simulation assembly 500 may be calibrated prior to performance of the method 1000. For example, practice weights may be applied to the pedal assembly 600 to calibrate the settings for the spring assembly 602 (e.g., to determine positioning for the first and second motion limiters 622 and 624 necessary to resist the compressive force supplied by various subjects and simulate a weightbearing condition).

At block 1002, a subject is positioned on the subject support 506 of a weightbearing simulation assembly 500. In embodiments, the weightbearing simulation assembly 500 may be disposed on the support platform 102, which may be positioned (e.g., via the actuator 128 as described with respect to FIG. 2) out of alignment with the imaging system 106 to facilitate positioning the subject on the subject support 506. Additionally, the subject support 506 may be rotatable about a first axis of rotation 520 to make it easier to position the subject on the weightbearing simulation assembly 500.

At block 1004, the weightbearing simulation assembly 500 is adjusted based on the subject and imaging requirements. For example, in embodiments, the distance 515 between the subject support 506 and the pedal assembly 600 is adjusted based on a length of the subject's leg to be imaged. In embodiments, the distance 515 is adjusted such that the subject's leg extends in the first direction (e.g., the x-direction depicted in FIG. 5A) and substantially the entirety of the subject's leg is in contact with the mounting surface 504 of the substrate 502. In embodiments, the subject support 506 may be tilted about the second axis of rotation 518 based on an imaging angle of the gantry 108. In embodiments, a relative angle between the first direction and the compression direction 626 of the pedal assembly 600 may be adjusted (e.g., by selecting a support position 682 of the adjustable support element 698) based on a portion of the subject's lower extremity being imaged. For example, in embodiments, to image an ankle of the subject, a first support position 682 is selected to place the compression direction 626 at a zero degree angle (e.g., parallel or substantially parallel) to the first direction. In embodiments, to image a forefoot of the subject, a second support position 682 is selected to place the compression direction 626 at a 30 degree angle relative to the first direction. In embodiments, to image a hindfoot of the subject, a third support position 682 is selected to place the compression direction 626 at a 45 degree angle relative to the first direction.

In embodiments adjustment of the weightbearing simulation assembly 500 also includes adjusting positions of the first and second motion limiters 622 and 624 between the contact plate 604 and the compression plate 606 based on a weight of the subject. As described herein, adjustment of the first and second motion limiters 622 and 624 determines a compressive force supplied via the first and second spring members 610 and 616 to the contact plate 604 when the subject supplies a load to the contact plate 604. The load supplied by the subject causes the contact plate 604 to contact ends 623 and 625 of the first and second motion limiters 622 and 624. As such, the positioning of the ends 623 and 625 determines the compressive force supplied via the first and second spring members 610 and 616. In embodiments, the spring assembly 602 is calibrated via placing a scale in contact with the contact plate 604 and using the scale to measure the compressive force supplied via the first and second spring members 610 and 616 as a function of the rotational position of the adjustment knob 670. In embodiments, adjustment of the weightbearing simulation assembly 500 includes rotating the adjustment knob 670 to a position such that the compressive force supplied via the first and second spring members 610 and 616 corresponds to approximately one half of the weight of the subject.

In a block 1006, the subject is secured to the weightbearing simulation assembly 500. For example, in embodiments, the subject's foot is secured to the pedal assembly 600 via placement of the subjects heel on the heel cup 694 and tightening the adjustable strap 696 around the subject's foot. Additionally, the subject may be secured to the subject support 506 via a shoulder strap or the like to assist the subject in supplying the load to the pedal assembly 600. At block 1008, the weightbearing simulation assembly 500 is positioned for imaging. For example, in embodiments, the actuator 128 of the support platform 102 is used to move the weightbearing simulation assembly 500 in the first direction towards the imaging system 106 such that the pedal assembly 600 is disposed within the opening 110 of the gantry 108 and the subject's lower extremity to be imaged is within a field of view of the imaging system 106.

In a block 1010, the subject is instructed to apply a force to the pedal assembly 600. For example, once the pedal assembly 600 is placed within the imaging system 106, the subject may be instructed to press her foot into the contact plate 604 so as to compress the first and second spring members 610 and 616 in the compression direction 626. The instructions may be automated (e.g., transmitted via a speaker system). In a block 1012, once the subject causes the contact plate 604 to contact the first and second motion limiters 622 and 624, thereby causing the first and second spring members 610 and 616 to exert a compressive force specifically tailored to the subject, an image is captured of the subject's lower extremity. The imaging system 106 may capture a CT scan or an MRI image of the subject's lower extremity while the lower extremity is in a weightbearing condition so as to capture three-dimensional structural measurements of the subject's lower extremity.

In view of the foregoing description, it should be appreciated that weightbearing simulation assemblies that are compatible with existing imaging systems may be used to capture three dimensional images of lower extremities of subjects while the lower extremities are in a loadbearing condition. The weightbearing simulation assemblies described herein include a pedal assembly with an adjustable spring assembly. The spring assembly disclosed herein is easily adjustable by altering the relative positioning of motion limiters disposed between a contact plate and a compression plates so as to limit the range of motion of the contact plate such that, when the spring assembly is placed in a loaded state by the subject, the spring assembly applies a compressive force to the contact plate that is specifically tailored to the subject. Moreover, a relative angle between the compressive force and an imaging axis of the imaging system may be adjusted to facilitate imaging multiple regions of the subject's foot. As such, the assemblies and methods described herein facilitate low cost load-bearing images at relatively low cost by providing compatibility with existing imaging systems.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

What is claimed is:

1. A weightbearing simulation assembly, comprising:
a substrate comprising a mounting surface extending in a first direction;
a subject support disposed on a first region of the mounting surface;
a pedal assembly disposed on a second region of the mounting surface, wherein the pedal assembly is spaced apart from the subject support by a distance in the first direction, the pedal assembly comprising a contact member; and
a device configured to provide instructions to a subject, the instructions direct the subject to apply a compressive force on the contact member that simulates an amount of pressure applied to lower extremities of the subject when the subject is standing,
wherein the contact member is configured to:
receive the compressive force from the subject in accordance with the instructions;
measure the compressive force; and
provide an indication that the compressive force corresponds to a weightbearing condition of the subject.

2. The weightbearing simulation assembly of claim 1, wherein the contact member comprises;
a contact plate facing the subject support; and
a sensor disposed on the contact plate and configured to measure the compressive force from the subject.

3. The weightbearing simulation assembly of claim 2, wherein the sensor comprises a pressure sensor configured to measure the compressive force from the subject.

4. The weightbearing simulation assembly of claim 3, wherein the contact member comprises a plurality of pressure sensors configured to measure pressure from the subject at a plurality of locations on the contact plate.

5. The weightbearing simulation assembly of claim 2, wherein the sensor comprises a force sensor configured to measure a total compressive force applied to the contact plate by the subject.

6. The weightbearing simulation assembly of claim 2, wherein the indication that the compressive force corresponds to the weightbearing condition for the subject comprises light or sound emitted by an indication generator coupled to the sensor.

7. The weightbearing simulation assembly of claim 1, wherein the contact member is configured to measure the compressive force by providing an adjustable amount of resistance to motion of the contact member.

8. The weightbearing simulation assembly of claim 7, wherein the amount of resistance to motion is adjustable electronically.

9. The weightbearing simulation assembly of claim 7, wherein the amount of resistance to motion is adjustable mechanically.

10. The weightbearing simulation assembly of claim 1, wherein the contact member comprises:
a spring assembly comprising a contact plate facing the subject support, a compression plate, and a first spring disposed between the contact plate and the compression plate, the spring extending in a compression direction; and
a motion limiter extending from the compression plate and comprising an end that is disposed between the compression plate and the contact plate to limit a range of motion of the contact plane in the compression direction.

11. The weightbearing simulation assembly of claim 10, wherein the indication that the compressive force to corresponds to the weightbearing condition for the subject comprises the contact plate contacting the end of the motion limiter.

12. The weightbearing simulation assembly of claim 1, further comprising:
a pedal support assembly disposed on the mounting surface, the pedal support assembly defining a cavity in which the contact member disposed; and
an adjustable support element for the pedal support assembly, the adjustable support element comprising a plurality of support positions selectable to adjust an orientation of the pedal support assembly to change a relative angle between the contact member and the mounting surface.

13. The weightbearing simulation assembly of claim 1, wherein the contact member comprises one or more rotation blocks movably coupled thereto for adjusting an orientation of the compressive force.

14. A subject imaging assembly, comprising:
- a support platform extending in a first direction, the support platform comprising an engagement element;
- an imaging system comprising a gantry, the gantry comprising an opening; and
- a weightbearing simulation assembly disposed on the support platform, the weightbearing simulation assembly comprising:
  - a substrate coupled to the engagement element of the support platform, the substrate comprising a mounting surface extending in the first direction;
  - a subject support disposed on a first region of the mounting surface, the subject support rotatable about an axis of rotation to facilitate positioning the subject support relative to the gantry;
  - a pedal assembly disposed on a second region of the mounting surface, wherein the pedal assembly is spaced apart from the subject support by a distance in the first direction, the pedal assembly comprising a contact member; and
  - a device configured to provide instructions to a subject, the instructions direct the subject to apply a compressive force on the contact member that simulates an amount of pressure applied to lower extremities of the subject when the subject is standing,
  - wherein the contact member is configured to:
    - receive the compressive force from the subject;
    - measure the compressive force; and
    - provide an indication that the compressive force to corresponds to a weightbearing condition for the subject.

15. The subject imaging assembly of claim 14, wherein the subject support comprises a seat having a first portion coupled to the mounting surface and a second portion extending at an angle to the first portion, wherein the first portion is coupled to the mounting surface via translation support mechanism so as to render the distance in the first direction between the subject support and the pedal assembly adjustable.

16. The subject imaging assembly of claim 15, wherein the first portion of the subject support is mounted to the translation support mechanism such that the first portion is rotatable about an axis of rotation in a second direction substantially perpendicular to the first direction so as to tilt the subject away from the pedal assembly.

17. The subject imaging assembly of claim 14, wherein the pedal assembly further comprises an adjustable support element for the pedal support assembly, the adjustable support element comprising a plurality of support positions selectable to adjust an orientation of the pedal support assembly to change a relative angle between the compression direction and the first direction.

18. The subject imaging assembly of claim 14, wherein the contact member is configured to measure the compressive force via one or more of:
- a sensor configured to measure the compressive force; and
- supplying a resistance to motion of the contact member.

19. A method of capturing an image of a lower extremity of a subject, the method comprising:
- positioning a subject on a subject support of a weight simulation assembly disposed on a support platform of an imaging system, wherein the weight simulation assembly comprises a substrate extending in the first direction, a subject support disposed on a first region of the substrate, and a pedal assembly disposed on a second region of the substrate, wherein the pedal assembly is spaced apart from the subject support by a distance in the first direction;
- adjusting a relative angle between a compression direction of a compressive force received from the subject and the first direction so as to adjust an angle of the lower extremity in the pedal assembly;
- positioning the weightbearing simulation assembly relative to a gantry of an imaging system such that the pedal assembly is disposed within an opening of the gantry;
- directing the subject to apply a compressive force on the contact member that simulates an amount of pressure applied to lower extremities of the subject when the subject is standing; and
- upon receiving an indication from the pedal assembly that the subject has applied the compressive force, capturing an image of the lower extremity using the imaging system.

20. The method of claim 19, further comprising adjusting an orientation of the lower extremity on the contact plate by adjusting a rotation block disposed on a contact plate of the pedal assembly.

* * * * *